(12) United States Patent
Flanigan et al.

(10) Patent No.: US 11,230,707 B2
(45) Date of Patent: *Jan. 25, 2022

(54) RECOMBINANT ADENO-ASSOCIATED VIRUS DELIVERY OF EXON 2-TARGETED U7SNRNA POLYNUCLEOTIDE CONSTRUCTS

(71) Applicant: RESEARCH INSTITUTE AT NATIONWIDE CHILDREN'S HOSPITAL, Columbus, OH (US)

(72) Inventors: Kevin Flanigan, Columbus, OH (US); Adeline Vulin-Chaffiol, Columbus, OH (US); Nicolas Wein, Columbus, OH (US)

(73) Assignee: RESEARCH INSTITUTE AT NATIONWIDE CHILDREN'S HOSPITAL, Columbus, OH (US)

(*) Notice: Subject to any disclaimer, the term of this patent is extended or adjusted under 35 U.S.C. 154(b) by 144 days.

This patent is subject to a terminal disclaimer.

(21) Appl. No.: 16/032,744

(22) Filed: Jul. 11, 2018

(65) Prior Publication Data

US 2019/0276822 A1    Sep. 12, 2019

Related U.S. Application Data

(63) Continuation of application No. 15/825,841, filed on Nov. 29, 2017, now abandoned, which is a continuation of application No. 14/785,769, filed as application No. PCT/US2014/034702 on Apr. 18, 2014, now Pat. No. 9,862,945.

(60) Provisional application No. 61/814,256, filed on Apr. 20, 2013.

(51) Int. Cl.
| | |
|---|---|
| *C12N 15/113* | (2010.01) |
| *A61K 48/00* | (2006.01) |
| *C12N 15/86* | (2006.01) |
| *C12N 15/11* | (2006.01) |
| *C12N 15/864* | (2006.01) |
| *C12N 7/00* | (2006.01) |
| *C07K 14/47* | (2006.01) |

(52) U.S. Cl.
CPC ........ *C12N 15/113* (2013.01); *A61K 48/005* (2013.01); *C07K 14/4708* (2013.01); *C12N 7/00* (2013.01); *C12N 15/111* (2013.01); *C12N 15/86* (2013.01); *C12N 15/8645* (2013.01); *C12N 2310/11* (2013.01); *C12N 2320/32* (2013.01); *C12N 2320/33* (2013.01); *C12N 2330/51* (2013.01); *C12N 2750/14132* (2013.01); *C12N 2750/14143* (2013.01); *C12N 2750/14171* (2013.01); *C12N 2750/14321* (2013.01); *C12N 2750/14333* (2013.01)

(58) Field of Classification Search
CPC ............. C12N 15/113; C12N 15/8645; C12N 2310/11; C12N 2750/14132; C07K 14/4708
See application file for complete search history.

(56) References Cited

U.S. PATENT DOCUMENTS

| | | |
|---|---|---|
| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,566,118 B1 | 5/2003 | Atkinson et al. |
| 7,282,199 B2 | 10/2007 | Gao et al. |
| 7,790,449 B2 | 9/2010 | Gao et al. |
| 9,862,945 B2 | 1/2018 | Flanigan et al. |
| 2006/0099616 A1 | 5/2006 | van Ommen et al. |
| 2011/0301218 A1* | 12/2011 | Bozzoni ............... C12N 15/111 514/44 A |
| 2012/0077860 A1 | 3/2012 | Garcia |
| 2012/0270925 A1 | 10/2012 | Wilton et al. |
| 2013/0045538 A1 | 2/2013 | Garcia et al. |
| 2013/0072541 A1 | 3/2013 | Garcia |

FOREIGN PATENT DOCUMENTS

| | | |
|---|---|---|
| EP | 2986632 B1 | 9/2018 |
| WO | WO-1995/13365 A1 | 5/1995 |
| WO | WO-1995/13392 A1 | 5/1995 |
| WO | WO-1996/17947 A1 | 6/1996 |
| WO | WO-1997/06243 A1 | 2/1997 |
| WO | WO-1997/08298 A1 | 3/1997 |
| WO | WO-1997/09441 A2 | 3/1997 |
| WO | WO-1997/21825 A1 | 6/1997 |
| WO | WO-1998/09657 A2 | 3/1998 |
| WO | WO-1999/11764 A2 | 3/1999 |
| WO | WO-2001/83692 | 11/2001 |

(Continued)

OTHER PUBLICATIONS

Aartsma-rus et al.: Antisense-induced exon skipping for duplications in Duchenne muscular dystrophy, *BMC Medical Genetics*, 8(1):43 (2007).
Alencastro et al., Targeted Exon Skipping To Correct Duplicated Exons In The Dystrophin Gene, 8th Australasian Gene Therapy Society Meeting, *J. Gene Med.*, 332 (2013).
Biggar et al., Deflazacort treatment of Duchenne muscular dystrophy, *J. Pediatr.*, 138:45-50 (2001).
Carter, Adeno-associated virus vectors, *Curr. Opin. Biotechnol.*, 3(5):533-9 (1992).

(Continued)

*Primary Examiner* — Richard A Schnizer
(74) *Attorney, Agent, or Firm* — Marshall, Gerstein & Borun LLP

(57) ABSTRACT

The present invention relates to recombinant adeno-associated virus (rAAV) delivery of polynucleotides for treating Duchenne Muscular Dystrophy resulting from the duplication of DMD exon 2. The invention provides rAAV products and methods of using the rAAV in the treatment of Duchenne Muscular Dystrophy.

17 Claims, 25 Drawing Sheets

Specification includes a Sequence Listing.

(56) References Cited

FOREIGN PATENT DOCUMENTS

| WO | 2003/74654 A2 | 9/2003 |
| WO | WO-2004/083432 A1 | 9/2004 |
| WO | WO-2009/101399 A1 | 8/2009 |
| WO | 2010/108126 A2 | 9/2010 |
| WO | 2011/057350 A1 | 5/2011 |
| WO | WO-2011/78797 A2 | 6/2011 |
| WO | 2011/113889 A1 | 9/2011 |
| WO | WO-2013/033407 A2 | 3/2013 |
| WO | 2014/172669 A1 | 10/2014 |

OTHER PUBLICATIONS

Cirak et al., Exon skipping and dystrophin restoration in patients with Duchenne muscular dystrophy after systemic phosphorodiamidate morpholino oligomer treatment: an open-label, phase 2, dose-escalation study, *Lancet*, 378:595-605 (2011).

Clark et al., A stable cell line carrying adenovirus-inducible rep and cap genes allows for infectivity titration of adeno-associated virus vectors, *Gene Therapy*, 3:1124-32 (1996).

Clark et al., Highly purified recombinant adeno-associated virus vectors are biologically active and free of detectable helper and wild-type viruses, *Hum. Gene Ther.*, 10(6):1031-9 (1999).

Cserjesi et al., Myogenin induces the myocyte-specific enhancer binding factor MEF-2 independently of other muscle-specific gene products, *Mol. Cell. Biol.*, 11:4854-62 (1991).

Dent et al., Improved molecular diagnosis of dystrophinopathies in an unselected clinical cohort, *Am. J. Med. Genet.*, 134(3): 295-8 (2005).

Exon Skipping Strategies for the Treatment of Duplication Mutations in Duchenne Muscular Dystrophy,<http://support.cureduchenne.org/site/P>Cure Duchenne (2012).

Flanigan et al., Mutational spectrum of DMD mutations in dystrophinopathy patients: application of modern diagnostic techniques to a large cohort, *Hum. Mutat.*, 30(12):1657-66 (2009).

Gao et al., Clades of Adeno-associated viruses are widely disseminated in human tissues, *J. Virol.*, 78: 6381-8 (2004).

GenBank Accession No. AF085716, Adeno-associated virus 5 DNA binding trs helicase (Rep22) and capsid protein (VP1) genes, complete cds, dated Feb. 9, 1999.

GenBank Accession No. NC_001401, Adeno-associated virus-2, complete genome, dated Dec. 2, 2014.

GenBank Accession No. NC_001829, Adeno-associated virus-4, complete genome, dated Jan. 28, 2010.

Genbank Accession No. NC_001862, Adeno-associated virus 6, complete genome, dated Jan. 12, 2004.

GenBank Accession No. NC_002077, Adeno-associated virus-1, complete genome, dated Mar. 11, 2010.

GenBank Accession Nos. AX753246, Sequence 1 from Patent EP1310571, dated Jun. 23, 2003.

GenBank Accession Nos. AX753249, Sequence 4 from Patent EP1310571, dated Jun. 23, 2003.

Goemans et al., Systemic administration of PRO051 in Duchenne's muscular dystrophy, *New Engl. J. Med.*, 364:1513-22 (2011).

Goyenvalle et al., Engineering Exon-Skipping Vectors Expressing U7 snRNA Constructs for Duchenne Muscular Dystrophy Gene Therapy, *Mus. Gene Ther.*, 306(5702):179-96 (2011).

Goyenvalle et al., Rescue of dystrophicmuscle through U7 snRNA-mediated exon skipping, *Sci.*, 306(5702):1796-9 (2004).

Goyenvalle et al., Rescue of severely affected dystrophin/utrophin-deficient mice through scAAV-U7snRNA-mediated exon skipping, *Hum. Molec. Gen.*, 21(11):2559-71 (2012).

Goyenvalle et al., Therapeutic approaches to muscular dystrophy, *Hum. Molec. Gen.*, 20(R1):R69-78 (2011).

Greer et al., Targeted Exon Skipping to Correct Exon Duplications in the Dystrophin Gene, *Molec. Ther. Nuc. Acids*, 3:e155 (2014).

Hakim et al., The passive mechanical properties of the extensor digitorum longus muscle are compromised in 2- to 20-mo-old mdx mice, *J. Appl. Physiol.*, 110:1656-63 (1985).

Hermonat et al., Use of adeno-associated virus as a mammalian DNA cloning vector: transduction of neomycin resistance into mammalian tissue culture cells, *Proc. Natl. Acad. Sci. USA*, 81:6466-70(1984).

Janssen et al., Utrophin deficiency worsens cardiac contractile dysfunction present in dystrophin-deficient mdx mice, *Am. J. Physiol. Heart Circ. Physiol.*, 289(6):H2373-8 (2005).

Johnson et al., Muscle creatine kinase sequence elements regulating skeletal and cardiac muscle expression in transgenic mice, *Mol. Cell. Biol.*, 9:3393-3399 (1989).

Laughlin et al., Cloning of infectious adeno-associated virus genomes in bacterial plasmids, *Gene.* 23:65-73 (1983).

Lebkowski et al., Adeno-associated virus: a vector system for efficient introduction and integration of DNA into a variety of mammalian cell types, *Mol. Cell. Biol.*, 7:3988-96-(1988).

De et al., High Levels of Persistent Expression of α1-Antitrypsin Mediated by the Nonhuman Primate Serotype rh. 10 Adeno-associated Virus despite preexisting immunity to Common Human Adeno-associated Viruses, *Molec. Ther.* 13(1):67-76 (2006).

Mader et al., A steroid-inducible promoter for the controlled overexpression of cloned genes in eukaryotic cells, *Proc. Natl. Acad. Sci. USA.* 90:5603-7 (1993).

Martin et al., Multi-confocal fluorescence correlation spectroscopy, *Am. J. Physiol. Cell. Physiol.*, 296:476-88 (2009).

McLaughlin et al., Adeno-associated virus general transduction vectors: analysis of proviral structures, *J. Virol.*, 62:1963 (1988).

Mendell et al., Randomized, double-blind six-month trial of prednisone in Duchenne's muscular dystrophy, *N. Engl. J. Med.*, 320:1592-7 (1989).

Mori et al., Two novel adeno-associated viruses from cynomolgus monkey: pseudotyping characterization of capsid protein, *Virology*, 330(2): 375-83 (2004).

Muscat et al., Multiple 5'-flanking regions of the human alpha-skeletal actin gene synergistically modulate muscle-specific expression, *Mol. Cell. Biol.*, 7:4089-99 (1987).

Muzyczka, Use of adeno-associated virus as a general transduction vector for mammalian cells, *Curr. Top. Microbiol. Immunol.* 158:97-129 (1992).

Paul et al., Increased viral titer through concentration of viral harvests from retroviral packaging lines, *Hum. Gene Ther.* 4:609-15 (1993).

Perrin et al., An experimental rabies vaccine produced with a new BHK-21 suspension cell culture process: use of serum-free medium and perfusion-reactor system, *Vaccine.* 13:1244-50 (1995).

Rabinowitz et al., Cross-packaging of a single adeno-associated virus (AAV) type 2 vector genome into multiple AAV serotypes enables transduction with broad specificity, *J. Virol.*, 76:791-801 (2002).

Rodino-Klapac et al., Persistent expression of FLAG-tagged micro dystrophin in nonhuman primates following intramuscular and vascular delivery, *Mol. Ther.*, 18(1):109-17 (2010).

Samulski et al., Cloning of adeno-associated virus into pBR322:rescue of intact virus from the recombinant plasmid in human cells, *Proc. Natl. Acad. Sci. USA.* 79:2077-81 (1982).

Samulski et al., Helper-free stocks of recombinant adeno-associated viruses: normal integration does not require viral gene expression, *J. Virol.* 63:3822-8 (1989).

Schenpp et al., Highly purified recombinant adeno-associated virus vectors. Preparation and quantitation, *Methods Mol. Med.*, 69:427-43 (2002).

Semenza et al., Hypoxia-inducible nuclear factors bind to an enhancer element located 3' to the human erythropoietin gene, *Proc. Natl. Acad. Sci. USA.* 88:5680-4 (1991).

Senapathy et al., Molecular cloning of adeno-associated virus variant genomes and generation of infectious virus by recombination in mammalian cells, *J. Biol. Chem.*, 259:4661-6 (1984).

Spurney et al., Preclinical drug trials in the mdx mouse: assessment of reliable and sensitive outcome measures, *Muscle & Nerve*, 39:591-602 (2009).

Srivastava et al., Nucleotide sequence and organization of the adeno-associated virus 2 genome, *J. Virol.* 45:555-64 (1983).

(56) References Cited

OTHER PUBLICATIONS

Tratschin et al., A Human parvovirus, Adeno-Associated Virus, as a Eucaryotic Vector: Transient Expression and Encapsidation of the Procaryotic Gene for Chloramphenicol Acetyltransferase, *Mol. Cell. Biol.* 4:2072 (1984).
Tratschin et al., Adeno-associated virus vector for high-frequency integration, expression, and rescue of genes in mammalian cells, *Mol. Cell. Biol.*, 5:3251 (1985).
Vulin et al., A New Mouse Model of DMD: A Tool for Therapeutic Development Directed at Exon Duplications, *Molec. Ther.*, 21(Suppl. 1)., (2013).
Wang et al., Recombinant AAV serotype 1 transduction efficiency and tropism in the murine brain, *Gene Ther.* 10:1528-34 (2003).
Weintraub et al., The myoD gene family: nodal point during specification of the muscle cell lineage, *Science.* 251:761-6 (1991).
White et al., Duplications in the DMD gene, *Hum. Mut.*, 27(9):938-45 (2006).
Xu et al., Postnatal overexpression of the CT GalNAc transferase inhibits muscular dystrophy in mdx mice without altering muscle growth or neuromuscular development: evidence for a utrophin-independent mechanism, *Neuromusc. Dis.*, 17:209-20 (2007).
Aartsma-Rus et al. Guidelines for Antisense Oligonucleotide Design and Insight Into Splice-modulating Mechanisms, Mol. Ther., 17(3): 548-553 (2009).
Aartsma-Rus et al., Targeted exon skipping as a potential gene correction therapy for Duchenne muscular dystrophy, Neuromuscular Disorders, 12: S71-S77 (2002).
Ameur et al., Total RNA sequencing reveals nascent transcription and widespread co-transcriptional splicing in the human brain, Nat. Struct. Mol. Biol., 18(12):1435-40 (2011).
Arechavala-Gomeza et al., Comparative analysis of antisense oligonucleotide sequences for targeted skipping of exon 51 during dystrophin pre-mRNA splicing in human muscle, Hum. Gene Ther., 18(9):798-810 (2007).
Beggs et al., Exploring the molecular basis for variability among patients with Becker muscular dystrophy: dystrophin gene and protein studies, Am. J. Hum. Genet., 49(1):54-67 (1991).
Betts et al., Prevention of exercised induced cardiomyopathy following Pip-PMO treatment in dystrophic mdx mice, Sci. Rep., 5:8986 (2015).
Chaouch et al., Immortalized skin fibroblasts expressing conditional MyoD as a renewable and reliable source of converted human muscle cells to assess therapeutic strategies for muscular dystrophies: validation of an exon-skipping approach to restore dystrophin in Duchenne muscular dystrophy cells, Hum. Gene Ther., 20(7):784-90 (2009).
Flanigan et al., Becker muscular dystrophy with widespread muscle hypertrophy and a non-sense mutation of exon 2, Neuromuscul. Disord., 23(2):192 (2013).
Flanigan et al., DMD Trp3X nonsense mutation associated with a founder effect in North American families with mild Becker muscular dystrophy, Neuromuscul. Disord., 19(11):743-8 (2009).
Gimona et al., Functional plasticity of CH domains, FEBS Lett., 513(1):98-106 (2002).
Goyenvalle et al., Engineering multiple U7snRNA constructs to induce single and multiexon-skipping for Duchenne muscular dystrophy, Mol. Ther., 20(6):1212-21 (2012).
Goyenvalle et al., Functional correction in mouse models of muscular dystrophy using exon-skipping tricyclo-DNA oligomers, Nat. Med., 21(3):270-5 (2015).
Gurvich et al., DMD exon 1 truncating point mutations: amelioration of phenotype by alternative translation initiation in exon 6, Hum. Mutat., 30(4):633-40 (2009).
Heald et al., Becker muscular dystrophy with onset after 60 years, Neurology, 44912:2388-90 (1994).
International Preliminary Report on Patentability received for PCT Patent Application No. PCT/US2014/034702, dated Oct. 29, 2015, 7 pages.

International Preliminary Report on Patentability received for PCT Patent Application No. PCT/US2015/044366, dated Feb. 23, 2017, 10 pages.
International Search Report and Written Opinion received for PCT Patent Application No. PCT/US2014/034702, dated Sep. 1, 2014, 10 pages.
International Search Report and Written Opinion received for PCT Patent Application No. PCT/US2015/044366, dated Feb. 1, 2016, 13 pages.
Kinali et al., Local restoration of dystrophin expression with the morpholino oligomer AVI-4658 in Duchenne muscular dystrophy: a single-blind, placebo-controlled, dose-escalation, proof-of-concept study, Lancet Neural., 8(10):918-28 (2009).
Mann et al., Improved antisense oligonucleotide induced exon skipping in the mdx mouse model of muscular dystrophy, J. Gene Med., 4(6):644-54 (2002).
Mendell et al., Eteplirsen for the treatment of Duchenne muscular dystrophy, Ann. Neural., 74(5):637-47 (2013).
Miura et al., IRES-mediated translation of utrophin A is enhanced by glucocorticoid treatment in skeletal muscle cells, PLoS One, 3(6):e2309 (2008).
Miura et al., The utrophin A 5'-untranslated region confers internal ribosome entry site-mediated translational control during regeneration of skeletal muscle fibers, J. Biol. Chem., 280(38):32997-3005 (2005).
Monaco et al., Dystrophin, the protein product of the Duchenne/Becker muscular dystrophy gene, Trends Biochem. Sci., 14910:412-5 (1989).
Tennyson et al., Stability of the human dystrophin transcript in muscle, Nucleic Acids Res., 24(15):3059-64 (1996).
Van Deutekom et al., Antisense-induced exon skipping restores dystrophin expression in DMD patient derived muscle cells, Hum. Mol. Gen., 10(15):1547-1554 (2001).
Van Deutekom et al., Local dystrophin restoration with antisense oligonucleotide PRO051, N. Engl. J. Med., 357(26):2677-86 (2007).
Vulin et al., Muscle function recovery in golden retriever muscular dystrophy after AAV1-U7 exon skipping, Mol. Ther., 20(11):2120-33 (2012).
Wein et al., Successful use of out-of-frame exon 2 skipping induces IRES-driven expression of the N-truncated dystrophin isoform: promising approach for treating other 5' dystrophin mutations, Mol. Ther., 22(Suppl. 1):S294-S295 (2014).
Wein et al., Translation from a DMD exon 5 IRES results in a functional dystrophin isoform that attenuates dystrophinopathy in humans and mice, Nat. Med., 20(9):992-1000 (2014).
Winnard et al., Characterization of translational frame exception patients in Duchenne/Becker muscular dystrophy, Hum. Mol. Genet., 2(6):737-44 (1993).
Winnard et al., Frameshift deletions of exons 3-7 and revertant fibers in Duchenne muscular dystrophy: mechanisms of dystrophin production, Am. J. Hum. Genet., 5691:158-66 (1995).
Witting et al., Becker muscular dystrophy with widespread muscle hypertrophy and a non-sense mutation of exon 2, Neuromuscul. Disord., 23(1):25-8 (2013).
Wood et al., RNA-targeted splice-correction therapy for neuromuscular disease, Brain, 133(Pt. 4):957-72 (2010).
Wu et al., Targeted Skipping of Human Dystrophin Exons in Transgenic Mouse Model Systemically for Antisense Drug Development, PLoS One, 6(5): 1-11 (2011).
Internet material, Cure Duchenne Supports Duchenne Duplication Mutation Research with Dr. Kevin Flanigan, 1-4 (2012).
Wein et al., A novel DMD IRES results in a functional N-truncated dystrophin, providing a potential route to therapy for patients with 5' mutations, Nat. Med. 20:992-1000 (2014) (including supplementary figures).
Chelly et al., Effect of dystrophin gene deletions on mRNA levels and processing in Duchenne and Becker muscular dystrophies, Cell. 63:1239-48 (1990).
Chelly et al., Illegitimate transcription. Application to the analysis of truncated transcripts of the dystrophin gene in nonmuscle cultured cells from Duchenne and Becker patients, J. Clin. Invest. 88:1161-6(1991).

(56) References Cited

OTHER PUBLICATIONS

Feener et al., Alternative splicing of human dystrophin mRNA generates isoforms at the carboxy terminus, *Nature*. 338:509-11 (1989).

* cited by examiner

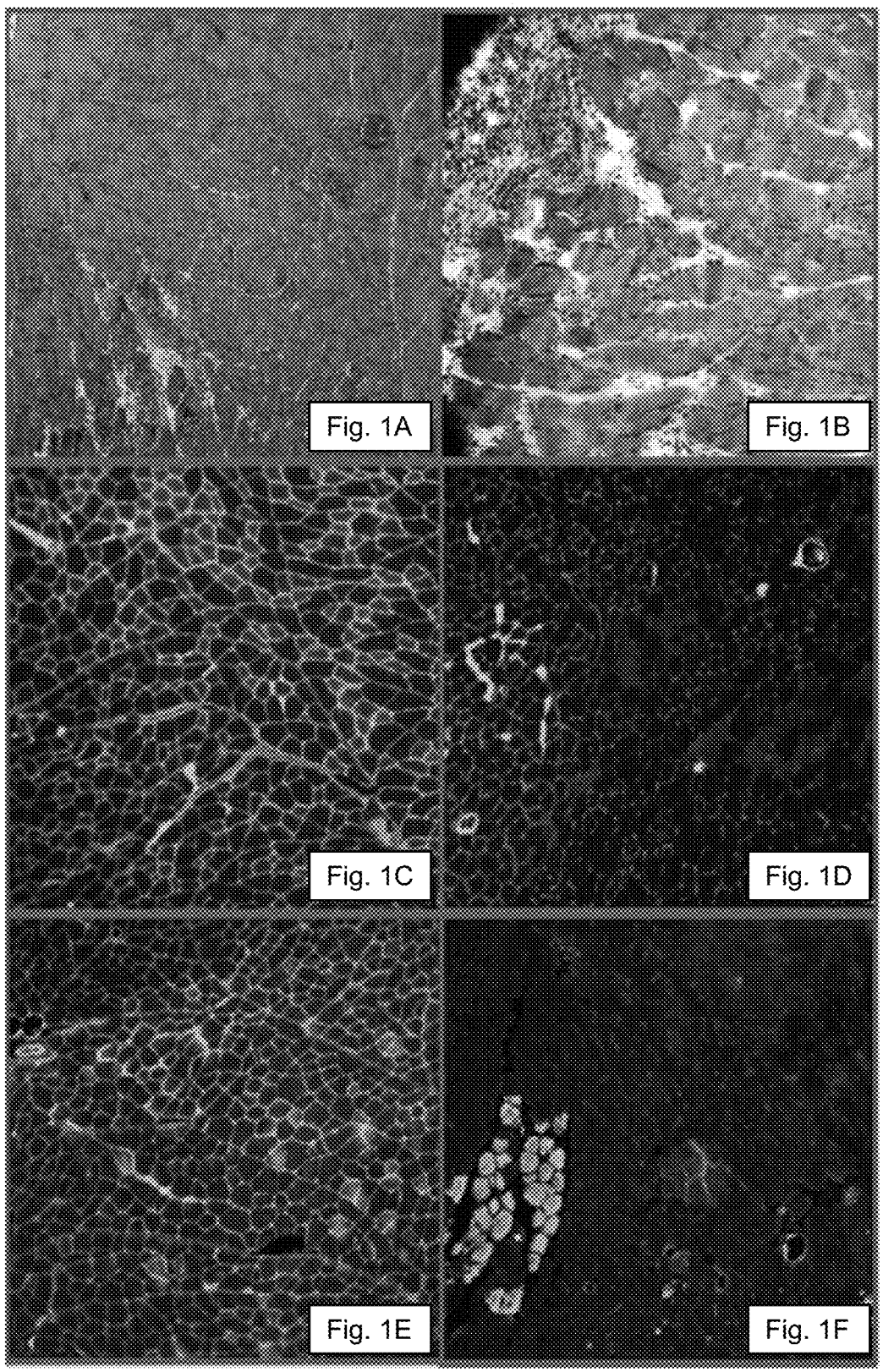

FIG. 2A
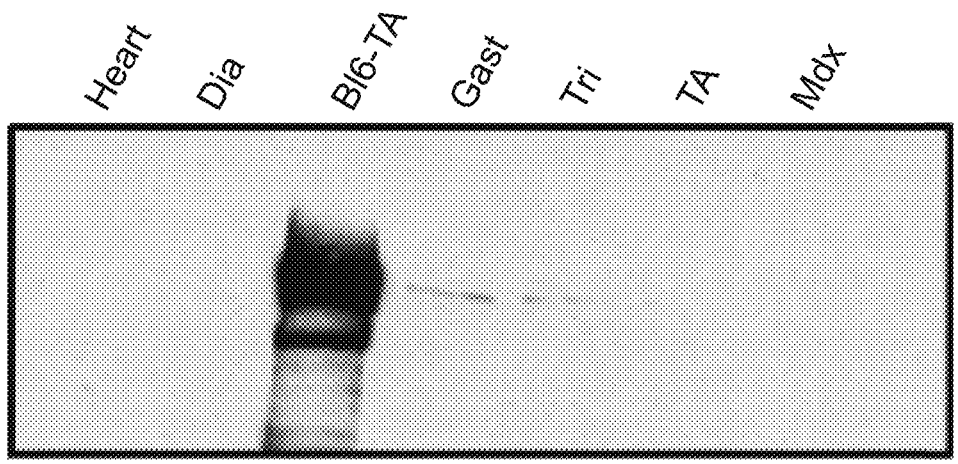
FIG. 2B
FIG. 2C
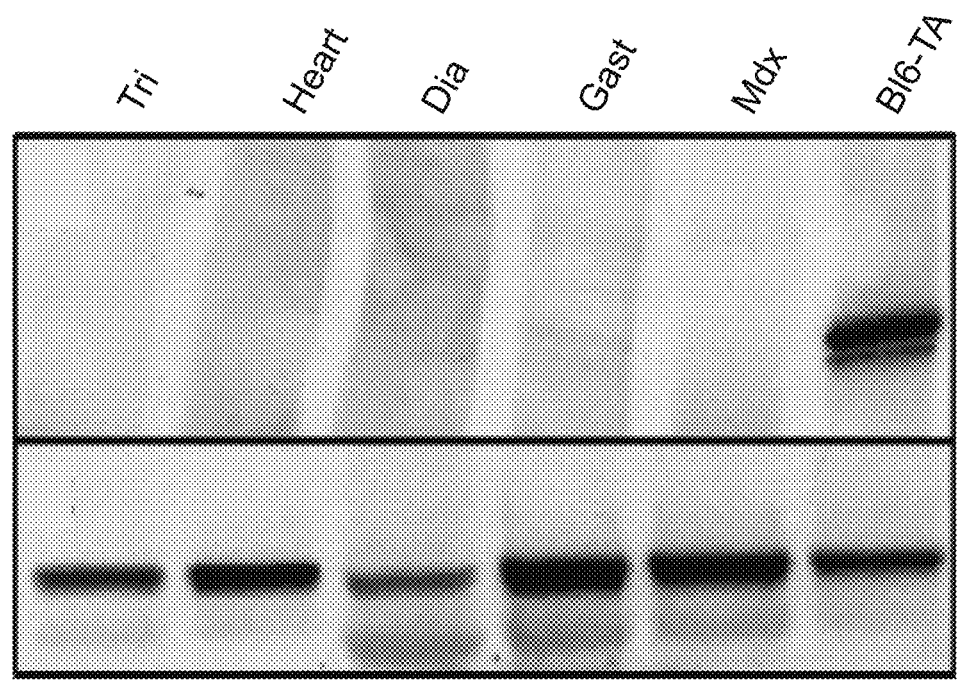

FIG. 6A
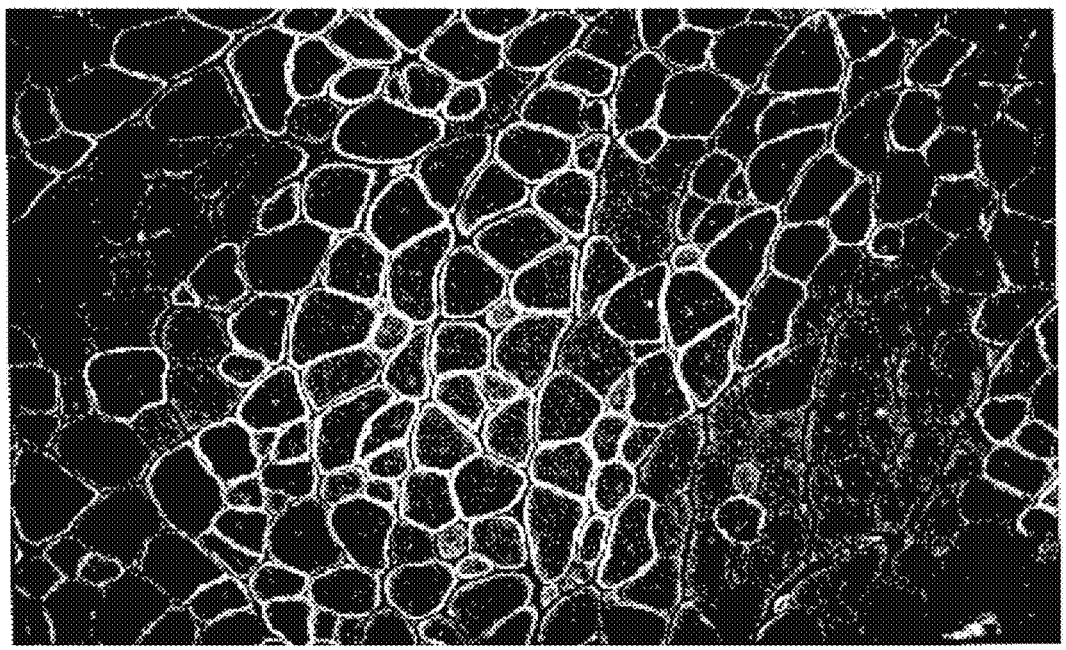
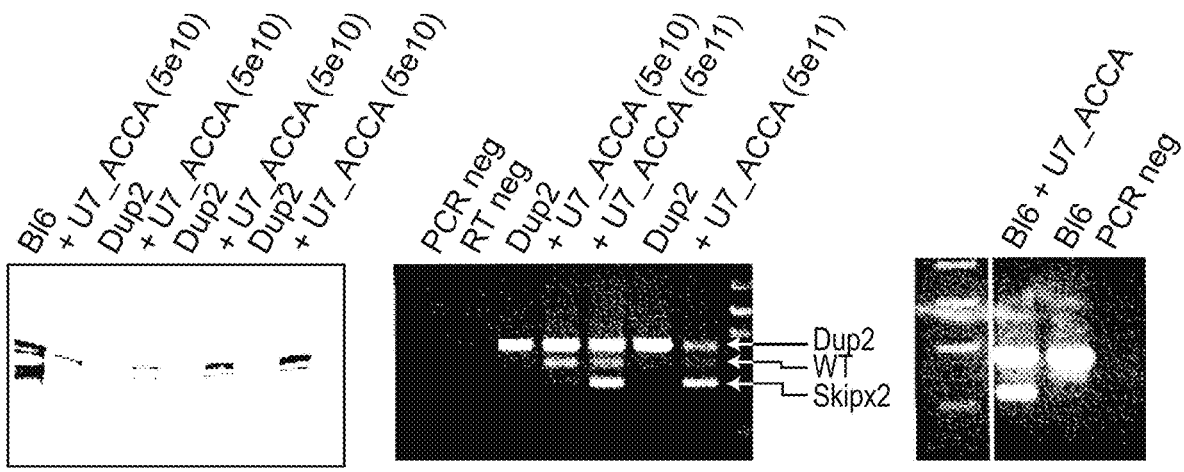
FIG. 6B    FIG. 6C    FIG. 6D

```
5'  CTCCATCACTAGGGGTAACCGCGAAGCGCCTCCCACGCTGCCGCGTCAGC
    +---+---+---+---+---+---+---+---+---+---+           50
    •────────D────────•

5'  GCTGACGTAAATTACGTCATAGGGGAGTGGTCCTGTATTAGCTGTCACGT
    +---+---+---+---+---+---+---+---+---+---+          100

5'  GAGTGCTTTTGCGACATTTTGCGACACCACGTGGCCATTCATGGTATATA
    +---+---+---+---+---+---+---+---+---+---+          150
                                            TAT_box 5'  TGGCCGAGTGAGCGAGCAGGATCTCCATTTTGACCGCGAAATTTGAACGA
    +---+---+---+---+---+---+---+---+---+---+          200
    ▪                    promoter 5'  GCAGCAGCCATGCCGGGCTTCTACGAGATCGTGCTTAAGGTGCCGAGCGA
    +---+---+---+---+---+---+---+---+---+---+          250
                          Rep 5'  CCTGGACGACCACCTGCCCGGCATTTCTCACTCGTTTCTGAACTCCGTCG
    +---+---+---+---+---+---+---+---+---+---+          300
                          Rep 5'  CAGAGAAGGAATGGGAGCTGCCCCCGGATTCTGACATGGATCGGAATCTG
    +---+---+---+---+---+---+---+---+---+---+          350
                          Rep 5'  ATTCAGCAGCCACCCCTCACCGTCCCCAGAAGCTACACCCCGACTTCCT
    +---+---+---+---+---+---+---+---+---+---+          400
                          Rep 5'  GGTCCAATGGCGCCGCGTGAGTAAGGCCCCGGAGGCCCTCTTCTTTGTTC
    +---+---+---+---+---+---+---+---+---+---+          450
                          Rep 5'  AGTTCGAGAAGGGCGAGTCCTACTTCCACCTCCATATTCTGGTAGAGACC
    +---+---+---+---+---+---+---+---+---+---+          500
                          Rep
```

Fig. 7A

```
5'  ACGGGGGTCAAATCCATGGTGCTGGGCCGCTTCCTGAGTCAGATTCGGA
                                                              550
                          Rep

5'  CAAGCTGGTGCAGACCATCTACCGCGGGATCGAGCCGACCCTGCCCAACT
                                                              600
                          Rep

5'  GGTTCGCGGTGACAAAGACGCGTAATGGCGCCGGAGGGGGGAACAAGGTG
                                                              650
                          Rep

5'  GTGGACGAGTGCTACATCCCCAACTACCTGCTGCCCAAGACTCAGCCCGA
                                                              700
                          Rep

5'  GCTGCAGTGGGCGTGGACTAACATGGAGGAGTATATAAGCGCGTGCTTGA
                                                              750
                          Rep
                                            TATA Box

5'  ACCTGGCCGAGCGCAAACGGCTCGTGGCGCAGCACCTGACCCACGTCAGC
                                                              800
                          Rep
        p1...1

5'  CAGACCCAGGAGCAGAACAAGGAGAATCTGAACCCGAATTCTGACGCGCC
                                                              850
                          Rep

5'  TGTCATCCGGTCAAAAACCTCCGCGCGCTACATGGAGCTGGTCGGGTGGC
                                                              900
                          Rep
                                                Rep 52 ORF
```

FIG. 7B

5' TGGTGGACCGGGGCATCACCTCCGAGAAGCAGTGGATCCAGGAGGACCAG 950
Rep
Rep 52 ORF

5' GCCTCGTACATCTCCTTCAACGCCGCCTCCAACTCGCGGTCTCAGATCAA 1000
Rep
Rep 52 ORF

5' GGCCGCGCTGGACAATGCCGGCAAGATCATGGCGCTGACCAAATCCGCGC 1050
Rep
Rep 52 ORF

5' CCGACTACCTGGTACCCCCCCTCTCCCCGCCCACATTAAATCCAACCCC 1100
Rep
Rep 52 ORF

5' ATCTACCGCATCCTGGAGCTGAATGGCTACGACCCTGCCTACGCCGGTTC 1150
Rep
Rep 52 ORF

5' CGTCTTTCTCGGCTGGGCCCAGAAAAAGTTTGGCAAAAGGAACACCATCT 1200
Rep
Rep 52 ORF

5' GGCTGTTTGGGCCGGCCACCACGGGCAAGACCAACATCGCGGAAGCCATC 1250
Rep
Rep 52 ORF

Fig. 7C

```
5'  GCCCACGCCGTGCCCTTCTACGGCTGCGTCAACTGGACCAATGAGAACTT
    +++++|+++++|+++++|+++++|+++++|+++++|+++++|+++++|+++++|+++++|  1300
                            Rep
                         Rep 52 ORF

5'  TCCCTTCAACCATTCCGTCGACAACATCGTCATCTCCTCCGACCACGGCA
    +++++|+++++|+++++|+++++|+++++|+++++|+++++|+++++|+++++|+++++|  1350
                            Rep
                         Rep 52 ORF

5'  AGATGACGGCCAAGGTCGTGGAGTCCGCCAAGGCCATTCTCGGCGGCAGC
    +++++|+++++|+++++|+++++|+++++|+++++|+++++|+++++|+++++|+++++|  1400
                            Rep
                         Rep 52 ORF

5'  AACGTCCGCGTGGACCAAAAGTGCAAGTCGTCCCCCAGATCCATCCCAC
    +++++|+++++|+++++|+++++|+++++|+++++|+++++|+++++|+++++|+++++|  1450
                            Rep
                         Rep 52 ORF

5'  CCCCGTGATCGTCACCTCCAACACCAACATGTGCGCCGTGATTGACGGGA
    +++++|+++++|+++++|+++++|+++++|+++++|+++++|+++++|+++++|+++++|  1500
                            Rep
                         Rep 52 ORF

5'  ACACCACCACCTTCGAGCACCAGCACCCGTTCCACGACCCGATCTTCAAA
    +++++|+++++|+++++|+++++|+++++|+++++|+++++|+++++|+++++|+++++|  1550
                            Rep
                         Rep 52 ORF

5'  TTTGAACTTACCCGCCGTCTGGAGCACGACTTTGGCAAGGTGACAAAGCA
    +++++|+++++|+++++|+++++|+++++|+++++|+++++|+++++|+++++|+++++|  1600
                            Rep
                         Rep 52 ORF
```

Fig. 7D

```
5'  GGAAGTCAAAGAGTTCTTCCGCTGGGCGCAGGATCACGTGACCGAGGTGG
                                                              1650
                         Rep
                      Rep 52 ORF

5'  CCCATCAGTTCTACCTCACAAAGGGTCCACCTAACAAACACCCCCCCC
                                                              1700
                         Rep
                      Rep 52 ORF

5'  GATGACGCGGATATAAGCGAGCCCAAGCGGGCCTGCCCCTCAGTCGCGGA
                                                              1750
                         Rep
                      Rep 52 ORF
          p40...ox

5'  TCCATCGACGTCAGACGCGGAAGGAGCTCCGGTGGACTTTGCCGACAGGT
                                                              1800
                         Rep
                      Rep 52 ORF
                                                      Sp...r

5'  ACCAAAACAAATGTTCTCGTCACGCGGGCATGCTTCAGATGCTGTTTCCC
                                                              1850
                         Rep
                      Rep 52 ORF

5'  TGCAAAACATGCGAGAGAATGAATCAGAATTTCAACATTTGCTTCACGCA
                                                              1900
                         Rep
                      Rep 52 ORF

5'  CGGGACCAGAGACTGTTCAGAATGTTTCCCTGGCGTGTCAGAATCTCAAC
                                                              1950
                         Rep
                      Rep 52 ORF
```

Fig. 7E

```
5'  CGGTCGTCAGAAAAAGACGTATCGGAAACTCTGTGCGATTCATCATCTG
    +++++|++++|++++|++++|++++|++++|++++|++++|++++|++++|  2000
                          Rep
    ▓▓▓▓▓▓▓▓▓▓▓▓▓▓▓▓▓▓ Rep 32 ORF ▓▓▓▓▓▓▓▓▓▓▓▓▓▓▓▓▓▓

5'  CTCCCCCGGCACCCCACATTCCTTCCTCGCCTCCCACCTCGTCAACGT
    +++++|++++|++++|++++|++++|++++|++++|++++|++++|++++|  2050
                          Rep
    ▓▓▓▓▓▓▓▓▓▓▓▓▓▓▓▓▓▓ Rep 52 ORF ▓▓▓▓▓▓▓▓▓▓▓▓▓▓▓▓▓▓

5'  GGACCTGGATGACTGTGTTTCTGAGCAATAAATGACTTAAACCAGGTATG
    +++++|++++|++++|++++|++++|++++|++++|++++|++++|++++|  2100
                          Rep
                                                   Cap
    ▓▓▓▓▓▓▓▓▓▓▓▓ Rep 52 ORF ▓▓▓▓▓▓▓▓▓▓▓▓
                                           R
                                                 sp..r

5'  GCTGCCGATGGTTATCTTCCAGATTGGCTCGAGGACAACCTCTCTGAGG
    +++++|++++|++++|++++|++++|++++|++++|++++|++++|++++|  2150
                          Rep
                          Cap
                        sp..r
                                                  R...

5'  CATTCGCGAGTGGTGGGACCTGAAACCTGGAGCCCCGAAACCCAAAGCCA
    +++++|++++|++++|++++|++++|++++|++++|++++|++++|++++|  2200
                          Cap

5'  ACCAGCAAAAGCAGGACAACCGCCCGGCGTCTGGTCCTTCCTGCCTACAAG
    +++++|++++|++++|++++|++++|++++|++++|++++|++++|++++|  2250
                          Cap

5'  TACCTCGGACCCTTCAACGGACTCGACAAGGGGGAGCCCGTCAACGCGGC
    +++++|++++|++++|++++|++++|++++|++++|++++|++++|++++|  2300
                          Cap
```

Fig. 7F

```
5'  CCACGCACCGGCCCTCGACCACCACAACCCCTACCACCACCACCTCCAAG
    +---+---+---+---+---+---+---+---+---+---+---+---+   2350
                            Cap

5'  CGGGTGACAATCCGTACCTGCGGTATAATCACGCCGACGCCGAGTTTCAG
    +---+---+---+---+---+---+---+---+---+---+---+---+   2400
                            Cap

5'  GAGCGTCTGCAAGAAGATACGTCTTTTGGGGGCAACCTCGGGCGCGCAGT
    +---+---+---+---+---+---+---+---+---+---+---+---+   2450
                            Cap

5'  CTTCCAGGCCAAAAAGCGGGTTCTCGAACCTCTGGGCCTGGTTGAATCGC
    +---+---+---+---+---+---+---+---+---+---+---+---+   2500
                            Cap

5'  CGGTTAAGACGGCTCCTGGAAAGAAGAGACCGGTAGAGCCATCACCCCAG
    +---+---+---+---+---+---+---+---+---+---+---+---+   2550
                            Cap
    VP1

5'  CGCTCTCCAGACTCCTCTACGGGCATCGGCAAGAAAGGCCAGCAGCCCGC
    +---+---+---+---+---+---+---+---+---+---+---+---+   2600
                            Cap

5'  AAAAAAGAGACTCAATTTTGGGCAGACTGGCGACTCAGAGTCAGTCCCCG
    +---+---+---+---+---+---+---+---+---+---+---+---+   2650
                            Cap

5'  ACCCTCAACCAATCGGAGAACCACCAGCAGGCCCCTCTGGTCTGGGATCT
    +---+---+---+---+---+---+---+---+---+---+---+---+   2700
                            Cap

5'  GGTACAATGGCTGCAGGCGGTGGCGCTCCAATGGCAGACAATAACGAAGG
    +---+---+---+---+---+---+---+---+---+---+---+---+   2750
                            Cap
    VP3
```

Fig. 7G

```
5'  CGCCGACGGAGTGGGTAGTTCCTCAGGAAATTGGCATTGCGATTCCACAT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  2800
                          Cap

5'  GGCTGGGCGACAGAGTCATCACCACCAGCACCCGCACCTGGGCCCTGCCC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  2850
                          Cap

5'  ACCTACAACAACCACCTCTACAAGCAAATCTCCAACGGGACCTCGGGAGG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  2900
                          Cap

5'  AAGCACCAACGACAACACCTACTTCGGCTACAGCACCCCCTGGGGGTATT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  2950
                          Cap

5'  TTGACTTCAACAGATTCCACTGCCACTTTTCACCACGTGACTGGCAGCGA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3000
                          Cap

5'  CTCATCAACAACAACTGGGGATTCCGGCCCAAGAGGCTCAACTTCAAGCT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3050
                          Cap

5'  CTTCAACATCCAAGTCAAGGAGGTCACGCAGAATGAAGGCACCAAGACCA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3100
                          Cap

5'  TCGCCAATAACCTTACCAGCACGATTCAGGTCTTTACGGACTCGGAATAC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3150
                          Cap

5'  CAGCTCCCGTACGTGCTCGGCTCGGCGCACCAGGGCTGCCTGCCTCCGTT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3200
                          Cap
```

Fig. 7H

```
5'  CCCGGCGGACGTCTTCATGATTCCTCAGTACGGGTACCTGACTCTGAACA
                                                        3250
                          Cap

5'  ATGGCAGTCAGGCTGTGGGCCGGTCGTCCTTCTACTGCCTGGAGTACTTT
                                                        3300
                          Cap

5'  CCTTCTCAAATGCTGAGAACGGGCAACAACTTTGAATTCAGCTACAACTT
                                                        3350
                          Cap

5'  CGAGGACGTGCCCTTCCACAGCAGCTACGCGCACAGCCAGAGCCTGGACC
                                                        3400
                          Cap

5'  GGCTGATGAACCCTCTCATCGACCAGTACTTGTACTACCTGTCCCGGACT
                                                        3450
                          Cap

5'  CAAAGCACGGGCGGTACTGCAGGAACTCAGCAGTTGCTATTTTCTCAGGC
                                                        3500
                          Cap

5'  CGGGCCTAACAACATGTCGGCTCAGGCCAAGAACTGGCTACCCGGTCCCT
                                                        3550
                          Cap

5'  GCTACCGGCAGCAACGCGTCTCCACGACACTGTCGCAGAACAACAACAGC
                                                        3600
                          Cap

5'  AACTTTGCCTGGACGGGTGCCACCAAGTATCATCTGAATGGCAGAGACTC
                                                        3650
                          Cap
```

Fig. 7I

```
5'  TCTGGTGAATCCTGGCGTTGCCATGGCTACCCACAAGGACGACGAAGAGC
                                                              3700
                        Cap

5'  GATTTTTTCCATCCAGCGGAGTCTTAATGTTTGGGAAACAGGGAGCTGGA
                                                              3750
                        Cap

5'  AAAGACAACGTGGACTATAGCAGCGTGATGCTAACCAGCGAGGAAGAAAT
                                                              3800
                        Cap

5'  AAAGACCACCAACCCAGTGGCCACAGAACAGTACGGCGTGGTGGCCGATA
                                                              3850
                        Cap

5'  ACCTGCAACAGCAAAACGCCGCTCCTATTGTAGGGGCCGTCAATAGTCAA
                                                              3900
                        Cap

5'  GGAGCCTTACCTGGCATGGTGTGGCAGAACCGGGACGTGTACCTGCAGGG
                                                              3950
                        Cap

5'  TCCCATCTGGGCCAAGATTCCTCATACGGACGGCAACTTTCATCCCTCGC
                                                              4000
                        Cap

5'  CGCTGATGGGAGGCTTTGGACTGAAGCATCCGCCTCCTCAGATCCTGATT
                                                              4050
                        Cap

5'  AAAAACACACCTGTTCCCGCGGATCCTCCGACCACCTTCAATCAGGCCAA
                                                              4100
                        Cap
```

Fig. 7J

```
5'  GCTGGCTTCTTTCATCACGCAGTACAGTACCGGCCAGGTCAGCGTGGAGA
    ++++++++++++++++++++++++++++++++++++++++++++++++++  4150
                            Cap

5'  TCGAGTGGGAGCTGCAGAAGGAGAACAGCAAACGCTGGAACCCAGAGATT
    ++++++++++++++++++++++++++++++++++++++++++++++++++  4200
                            Cap

5'  CAGTACACTTCCAACTACTACAAATCTACAAATGTGGACTTTGCTGTCAA
    ++++++++++++++++++++++++++++++++++++++++++++++++++  4250
                            Cap

5'  TACTGAGGGTACTTATTCCGAGCCTCGCCCCATTGGCACCCGTTACCTCA
    ++++++++++++++++++++++++++++++++++++++++++++++++++  4300
                            Cap

5'  CCCGTAATCTGTAATTACATGTTAATCAATAAACCGGTTAATTCGTTTCA
    ++++++++++++++++++++++++++++++++++++++++++++++++++  4350
         Cap
              C              poly_nal 5'  GTTGAACTTTGGTCTCCTGTCCTTCTTATCTTATCGGTTACCATAGAAAC
    ++++++++++++++++++++++++++++++++++++++++++++++++++  4400

5'  TGGTTACTTATTAACTGCTTGGTGCGCTTCGCGATAAAGACTTACGTCA
    ++++++++++++++++++++++++++++++++++++++++++++++++++  4450

5'  TCGGGTTACCCCTAGTGATGGA
    ++++++++++++++++++++++  4472
         ←——— D ———→
```

Fig. 7K

Legend:

ATCG: inverted terminal sequence (ITR)

ATCG:U7-Along (antisense sequence in capital letters) (first copy)
(SEQ ID NO: 7 = CTCCAAAAATTTAGATGAAAGAGAAGATCTTCAAAAGAAAAC)

ATCG: U7-C (antisense sequence in capital letters)(first copy)
(SEQ ID NO: 8 = CTCCAAAAATTGCACAATTTTCTAAGGTAAGAATTT)

ATCG: U7-C (antisense sequence in capital letters)(second copy)
(SEQ ID NO: 8 = CTCCAAAAATTGCACAATTTTCTAAGGTAAGAATTT)

ATCG:U7-Along (antisense sequence in capital letters) (second copy)
(SEQ ID NO: 7 = CTCCAAAAATTTAGATGAAAGAGAAGATCTTCAAAAGAAAAC)

ATCG: inverted terminal sequence 3'(ITR)

ctgcgcgctcgctcgctcactgaggccgcccgggcaaagcccgggcgtcgggcgacctttgtcgcccggcctcagtgagcgagcgag
cgcgcagagaggagtggggttgtacacatacgcgttttcctaggaaaccagagaaggatcaaagcccctctcacacaccggggagcgg
ggaagagaactgttttgctttcattgtagaccagtgaaattgggagggttttccgaccgaagtcagaaaacctgCTCCAAAAATTt
agATGAAAGAGAAGATCTTCAAAAGAAAACttgcggaagtgcgtctgtagcgagccagggAaggacatcaa
ctccactttcgatgaggtgagatcaaggtgccattccacaccccctccactgatatgtgaatcacaaagcacagttccttattcggttcgataa
acaatattctaaaagactattaaaaccgctcgttcttgagtttgtgaccgcttgtaaaggctatgcaaatgagTcagtgctgattggctgaaaa
cagccaatcacagctcctatgttgttaTCTAGCcacatacgcgttttcctaggaaaccagagaaggatcaaagcccctctcacacacg
gggagcggggaagagaactgttttgctttcattgtagaccagtgaaattgggagggttttccgaccgaagtcagaaaacctgCTCCA
AAAATTGCACAATTTTCTAAGGTAAGAATTTgcggaagtgcgtctgtagcgagccagggAaggacatcaa
ctccactttcgatgaggtgagatcaaggtgccattccacaccccctccactgatatgtgaatcacaaagcacagttccttattcggttcgataa
acaatattctaaaagactattaaaaccgctcgttcttgagtttgtgaccgcttgtaaaggctatgcaaatgagTcagtgctgattggctgaaaa
cagccaatcacagctcctatgttgttaTCTAGCcacatacgcgttttcctaggaaaccagagaaggatcaaagcccctctcacacacg
gggagcggggaagagaactgttttgctttcattgtagaccagtgaaattgggagggttttccgaccgaagtcagaaaacctgCTCCA
AAAATTGCACAATTTTCTAAGGTAAGAATTTgcggaagtgcgtctgtagcgagccagggAaggacatcaa
ctccactttcgatgaggtgagatcaaggtgccattccacaccccctccactgatatgtgaatcacaaagcacagttccttattcggttcgataa
acaatattctaaaagactattaaaaccgctcgttcttgagtttgtgaccgcttgtaaaggctatgcaaatgagTcagtgctgattggctgaaaa
cagccaatcacagctcctatgttgttaTCTAGCcacatacgcgttttcctaggaaaccagagaaggatcaaagcccctctcacacacg
gggagcggggaagagaactgttttgctttcattgtagaccagtgaaattgggagggttttccgaccgaagtcagaaaacctgCTCCA
AAAATTtagATGAAAGAGAAGATCTTCAAAAGAAAACttgcggaagtgcgtctgtagcgagccagggA
aggacatcaactccactttcgatgaggtgagatcaaggtgccattccacaccccctccactgatatgtgaatcacaaagcacagttccttatt
cggttcgataaacaatattctaaaagactattaaaaccgctcgttcttgagtttgtgaccgcttgtaaaggctatgcaaatgagTcagtgctga
ttggctgaaaacagccaatcacagctcctatgttgttatctagagcatggctacgtagataagtagcatggcgggttaatcattaactacaagg
aacccctagtgatggagttggccactccctctctgcgcgctcgctcgtcactgaggccgggcgaccaaaggtcgcccgacgcccgggct
ttgcccgggcggcctcagtgagcgagcgagcgcgccagc

FIGURE 9

SEQUENCE LISTING

```
<160> NUMBER OF SEQ ID NOS: 8

<210> SEQ ID NO 1
<211> LENGTH: 4472
<212> TYPE: DNA
<213> ORGANISM: Adeno-associated virus

<400> SEQUENCE: 1
ctccatcact aggggtaacc gcgaagcgcc tcccacgctg ccgcgtcagc gctgacgtaa      60
attacgtcat aggggagtgg tcctgtatta gctgtcacgt gagtgctttt gcgacatttt     120
gcgacaccac gtggccattc atggtatata tggccgagtg agcgagcagg atctccattt     180
tgaccgcgaa atttgaacga gcagcagcca tgccgggctt ctacgagatc gtgcttaagg     240
tgccgagcga cctggacgag cacctgccgg gcatttctga ctcgtttgtg aactgggtgg     300
cagagaagga atgggagctg cccccggatt ctgacatgga tcggaatctg attgagcagg     360 caccctgac cgtggccgag aagctacagc gcgacttcct ggtccaatgg cgccgcgtga     420
gtaaggcccc ggaggccctc ttctttgttc agttcgagaa gggcgagtcc tacttccacc     480
tccatattct ggtagagacc acgggggtca aatccatggt gctgggccgc ttcctgagtc     540
agattcggga caagctggtg cagaccatct accgcgggat cgagccgacc ctgcccaact     600
ggttcgcggt gacaaagacg cgtaatggcg ccggaggggg gaacaaggtg gtggacgagt     660
gctacatccc caactacctg ctgcccaaga ctcagcccga gctgcagtgg gcgtggacta     720
acatggagga gtatataagc gcgtgcttga acctggccga gcgcaaacgg ctcgtggcgc     780
```

```
agcacctgac ccacgtcagc cagacccagg agcagaacaa ggagaatctg aacccgaatt    840
ctgacgcgcc tgtcatccgg tcaaaaacct ccgcgcgcta catggagctg gtcgggtggc    900
tggtggaccg gggcatcacc tccgagaagc agtggatcca ggaggaccag gcctcgtaca    960
tctccttcaa cgccgcctcc aactcgcggt ctcagatcaa ggccgcgctg acaatgccg    1020 gcaagatcat ggcgctgacc aaatccgcgc ccgactacct ggtaggcccc gctctgcccg    1080
cggacattaa atccaaccgc atctaccgca tcctggagct gaatggctac gaccctgcct    1140
acgccggttc cgtctttctc ggctgggccc agaaaaagtt tggcaaaagg aacaccatct    1200
ggctgtttgg gccggccacc acgggcaaga ccaacatcgc ggaagccatc gcccacgccg    1260
tgcccttcta cggctgcgtc aactggacca atgagaactt tcccttcaac gattgcgtcg    1320
acaagatggt gatctggtgg gaggagggca agatgacggc caaggtcgtg gagtccgcca    1380
aggccattct cggcggcagc aaggtgcgcg tggaccaaaa gtgcaagtcg tccgcccaga    1440
tcgatcccac ccccgtgatc gtcacctcca acaccaacat gtgcgccgtg attgacggga    1500
acagcaccac cttcgagcac cagcagccgt tgcaggaccg gatgttcaaa tttgaactta    1560
cccgccgtct ggagcacgac tttggcaagg tgacaaagca ggaagtcaaa gagttcttcc    1620
gctgggcgca ggatcacgtg accgaggtgg cgcatgagtt ctacgtcaga aagggtggag    1680
ctaacaaaag acccgccccc gatgacgcgg atataagcga gcccaagcgg gcctgcccct    1740
cagtcgcgga tccatcgacg tcagacgcgg aaggagctcc ggtggacttt gccgacaggt    1800
accaaaacaa atgttctcgt cacgcgggca tgcttcagat gctgtttccc tgcaaaacat    1860
gcgagagaat gaatcagaat ttcaacattt gcttcacgca cgggaccaga gactgttcag    1920
aatgtttccc tggcgtgtca gaatctcaac cggtcgtcag aaaaaagacg tatcggaaac    1980
tctgtgcgat tcatcatctg ctggggcggg cacccgagat tgcttgctcg gcctgcgacc    2040
tggtcaacgt ggacctggat gactgtgttt ctgagcaata aatgacttaa accaggtatg    2100
gctgccgatg gttatcttcc agattggctc gaggacaacc tctctgaggg cattcgcgag    2160
tggtgggacc tgaaacctgg agccccgaaa cccaaagcca accagcaaaa gcaggacaac    2220
ggccggggtc tggtgcttcc tggctacaag tacctcggac ccttcaacgg actcgacaag    2280
ggggagcccg tcaacgcggc ggacgcagcg gccctcgagc acgacaaggc ctacgaccag    2340
cagctccaag cgggtgacaa tccgtacctg cggtataatc acgccgacgc cgagtttcag    2400
gagcgtctgc aagaagatac gtcttttggg ggcaacctcg ggcgcgcagt cttccaggcc    2460
aaaaagcggg ttctcgaacc tctgggcctg gttaatcgc cggttaagac ggctcctgga    2520
aagaagagac cggtagagcc atcacccag cgctctccag actcctctac gggcatcggc    2580
aagaaaggcc agcagcccgc aaaaaagaga ctcaattttg gcagactgg cgactcagag    2640 tcagtcccg accctcaacc aatcggagaa ccaccagcag gcccctctgg tctgggatct    2700
ggtacaatgg ctgcaggcgg tggcgctcca atggcagaca ataacgaagg cgccgacgga    2760
gtgggtagtt cctcaggaaa ttggcattgc gattccacat ggctgggcga cagagtcatc    2820
accaccagca cccgcacctg ggccctgccc acctacaaca accacctcta caagcaaatc    2880
tccaacggga cctcggagg aagcaccaac gacaacacct acttcggcta cagcaccccc    2940
tgggggtatt ttgacttcaa cagattccac tgccactttt caccacgtga ctggcagcga    3000
ctcatcaaca caactggggg attccggccc aagaggctca acttcaagct cttcaacatc    3060
caagtcaagg aggtcacgca gaatgaaggc accaagacca tcgccaataa ccttaccagc    3120
acgattcagg tctttacgga ctcggaatac cagctcccgt acgtgctcgg ctcggcgcac    3180
```

```
cagggctgcc tgcctccgtt cccggcggac gtcttcatga ttcctcagta cgggtacctg    3240
actctgaaca atggcagtca ggctgtgggc cggtcgtcct tctactgcct ggagtacttt    3300
ccttctcaaa tgctgagaac gggcaacaac tttgaattca gctacaactt cgaggacgtg    3360
cccttccaca gcagctacgc gcacagccag agcctggacc ggctgatgaa ccctctcatc    3420
gaccagtact tgtactacct gtcccggact caaagcacgg gcggtactgc aggaactcag    3480
cagttgctat tttctcaggc cgggcctaac aacatgtcgg ctcaggccaa gaactggcta    3540
cccggtccct gctaccggca gcaacgcgtc tccacgacac tgtcgcagaa caacaacagc    3600
aactttgcct ggacgggtgc caccaagtat catctgaatg gcagagactc tctggtgaat    3660
cctggcgttg ccatggctac ccacaaggac gacgaagagc gattttttcc atccagcgga    3720
gtcttaatgt ttgggaaaca gggagctgga aaagacaacg tggactatag cagcgtgatg    3780
ctaaccagcg aggaagaaat aaagaccacc aacccagtgg ccacagaaca gtacggcgtg    3840
gtggccgata acctgcaaca gcaaaacgcc gctcctattg taggggccgt caatagtcaa    3900
ggagccttac ctggcatggt gtggcagaac cgggacgtgt acctgcaggg tcccatctgg    3960
gccaagattc ctcatacgga cggcaacttt catccctcgc cgctgatggg aggctttgga    4020
ctgaagcatc cgcctcctca gatcctgatt aaaaacacac tgttcccgc ggatcctccg    4080 accaccttca ctaaggccaa gctggcttct ttcatcacgc agtacagtac cggccaggtc    4140
agcgtggaga tcgagtggga gctgcagaag gagaacagca acgctggaa cccagagatt    4200 cagtacactt ccaactacta caaatctaca aatgtggact tgctgtcaa tactgagggt    4260 acttattccg agcctcgccc cattggcacc cgttacctca cccgtaatct gtaattacat    4320
gttaatcaat aaaccggtta attcgtttca gttgaacttt ggtctcctgt ccttcttatc    4380
ttatcggtta ccatagaaac tggttactta ttaactgctt ggtgcgcttc gcgataaaag    4440
acttacgtca tcgggttacc cctagtgatg ga                                   4472
```

<210> SEQ ID NO 2
<211> LENGTH: 2052
<212> TYPE: DNA
<213> ORGANISM: Adeno-associated virus
<220> FEATURE:
<221> NAME/KEY: misc_feature
<222> LOCATION: (1)..(88)
<223> OTHER INFORMATION: Inverted Terminal Sequence (ITR)
<220> FEATURE:
<221> NAME/KEY: misc_feature
<222> LOCATION: (89)..(365)
<223> OTHER INFORMATION: U7-Along
<220> FEATURE:
<221> NAME/KEY: misc_feature
<222> LOCATION: (525)..(806)
<223> OTHER INFORMATION: U7-C
<220> FEATURE:
<221> NAME/KEY: misc_feature
<222> LOCATION: (961)..(1242)
<223> OTHER INFORMATION: U7-C
<220> FEATURE:
<221> NAME/KEY: misc_feature
<222> LOCATION: (1397)..(1678)
<223> OTHER INFORMATION: U7-Along
<220> FEATURE:
<221> NAME/KEY: misc_feature
<222> LOCATION: (1830)..(2052)
<223> OTHER INFORMATION: Inverted Terminal Sequence 3' (ITR)

<400> SEQUENCE: 2

```
ctgcgcgctc gctcgctcac tgaggccgcc cgggcaaagc ccgggcgtcg ggcgaccttt    60
```

-continued

```
ggtcgcccgg cctcagtgag cgagcgagcg cgcagagagg gagtggggtt gtacacatac     120
gcgtttccta ggaaaccaga gaaggatcaa agcccctctc acacaccggg gagcggggaa     180
gagaactgtt ttgctttcat tgtagaccag tgaaattggg aggggttttc cgaccgaagt     240
cagaaaacct gctccaaaaa tttagatgaa agagaagatc ttcaaaagaa aacttgcgga     300
agtgcgtctg tagcgagcca gggaaggaca tcaactccac tttcgatgag ggtgagatca     360
aggtgccatt tccacacccc tccactgata tgtgaatcac aaagcacagt tccttattcg     420
gttcgataaa caatattcta aaagactatt aaaaccgctc gtttcttgag tttgtgaccg     480
cttgtaaagg ctatgcaaat gagtcagtgc tgattggctg aaaacagcca atcacagctc     540
ctatgttgtt atctagccac atacgcgttt cctaggaaac cagagaagga tcaaagcccc     600
tctcacacac cggggagcgg ggaagagaac tgttttgctt tcattgtaga ccagtgaaat     660
tgggaggggt tttccgaccg aagtcagaaa acctgctcca aaaattgcac aattttctaa     720
ggtaagaatt tgcggaagtg cgtctgtagc gagccaggga aggacatcaa ctccactttc     780
gatgagggtg agatcaaggt gccatttcca caccctcca ctgatatgtg aatcacaaag     840
cacagttcct tattcggttc gataaacaat attctaaaag actattaaaa ccgctcgttt     900
cttgagtttg tgaccgcttg taaaggctat gcaaatgagt cagtgctgat tggctgaaaa     960
cagccaatca cagctcctat gttgttatct agccacatac gcgtttccta ggaaaccaga    1020
gaaggatcaa agcccctctc acacaccggg gagcggggaa gagaactgtt ttgctttcat    1080
tgtagaccag tgaaattggg aggggttttc cgaccgaagt cagaaaacct gctccaaaaa    1140
ttgcacaatt ttctaaggta agaatttgcg gaagtgcgtc tgtagcgagc cagggaagga    1200
catcaactcc actttcgatg agggtgagat caaggtgcca tttccacacc cctccactga    1260
tatgtgaatc acaaagcaca gttccttatt cggttcgata acaatattc taaaagacta    1320 ttaaaaccgc tcgtttcttg agtttgtgac cgcttgtaaa ggctatgcaa atgagtcagt    1380
gctgattggc tgaaaacagc caatcacagc tcctatgttg ttatctagcc acatacgcgt    1440
ttcctaggaa accagagaag gatcaaagcc cctctcacac accggggagc ggggaagaga    1500
actgttttgc tttcattgta gaccagtgaa attgggaggg gttttccgac cgaagtcaga    1560
aaacctgctc caaaaattta gatgaaagag aagatcttca aaagaaaact gcggaagtg    1620 cgtctgtagc gagccaggga aggacatcaa ctccactttc gatgagggtg agatcaaggt    1680
gccatttcca caccctcca ctgatatgtg aatcacaaag cacagttcct tattcggttc    1740
gataaacaat attctaaaag actattaaaa ccgctcgttt cttgagtttg tgaccgcttg    1800
taaaggctat gcaaatgagt cagtgctgat tggctgaaaa cagccaatca cagctcctat    1860
gttgttatct agagcatggc tacgtagata agtagcatgg cgggttaatc attaactaca    1920
aggaacccct agtgatggag ttggccactc cctctctgcg cgctcgctcg ctcactgagg    1980
ccgggcgacc aaaggtcgcc cgacgcccgg gctttgcccg ggcggcctca gtgagcgagc    2040
gagcgcgcca gc                                                        2052
```

<210> SEQ ID NO 3
<211> LENGTH: 28
<212> TYPE: DNA
<213> ORGANISM: Adeno-associated virus

<400> SEQUENCE: 3

```
tcaaaagaaa acattcacaa aatgggta                                         28
```

```
<210> SEQ ID NO 4
<211> LENGTH: 31
<212> TYPE: DNA
<213> ORGANISM: Adeno-associated virus

<400> SEQUENCE: 4
gttttctttt gaagatcttc tctttcatct a                                    31

<210> SEQ ID NO 5
<211> LENGTH: 19
<212> TYPE: DNA
<213> ORGANISM: Adeno-associated virus

<400> SEQUENCE: 5
agatcttctc tttcatcta                                                  19

<210> SEQ ID NO 6
<211> LENGTH: 23
<212> TYPE: DNA
<213> ORGANISM: Adeno-associated virus

<400> SEQUENCE: 6 gcacaattt ctaaggtaag aat                                              23

<210> SEQ ID NO 7
<211> LENGTH: 42
<212> TYPE: DNA
<213> ORGANISM: Adeno-associated virus

<400> SEQUENCE: 7
ctccaaaaat ttagatgaaa gagaagatct tcaaaagaaa ac                        42

<210> SEQ ID NO 8
<211> LENGTH: 36
<212> TYPE: DNA
<213> ORGANISM: Adeno-associated virus

<400> SEQUENCE: 8
ctccaaaaat tgcacaattt tctaaggtaa gaattt                               36
```

RECOMBINANT ADENO-ASSOCIATED VIRUS DELIVERY OF EXON 2-TARGETED U7SNRNA POLYNUCLEOTIDE CONSTRUCTS

This application claims the benefit of the filing date of U.S. Provisional Patent Application No. 61/814,256 filed Apr. 19, 2013, which is incorporated by reference herein in its entirety.

FIELD OF THE INVENTION

The present invention relates to recombinant adeno-associated virus (rAAV) delivery of polynucleotides for treating Duchenne Muscular Dystrophy resulting from the duplication of DMD exon 2. The invention provides rAAV products and methods of using the rAAV in the treatment of Duchenne Muscular Dystrophy.

INCORPORATION BY REFERENCE OF THE SEQUENCE LISTING

This application contains, as a separate part of disclosure, a Sequence Listing in computer-readable form (filename: 47699PCT_SeqListing.txt; 10,162 bytes—ASCII text file, created 18 Apr. 2014) which is incorporated by reference herein in its entirety.

BACKGROUND

Muscular dystrophies (MDs) are a group of genetic diseases. The group is characterized by progressive weakness and degeneration of the skeletal muscles that control movement Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

One form of MD is Duchenne Muscular Dystrophy (DMD). It is the most common severe childhood form of muscular dystrophy affecting 1 in 5000 newborn males. DMD is caused by mutations in the DMD gene leading to absence of dystrophin protein (427 KDa) in skeletal and cardiac muscles, as well as GI tract and retina. Dystrophin not only protects the sarcolemma from eccentric contractions, but also anchors a number of signaling proteins in close proximity to sarcolemma. Many clinical cases of DMD are linked to deletion mutations in the DMD gene. Despite many lines of research following the identification of the DMD gene, treatment options are limited. Corticosteroids are clearly beneficial but even with added years of ambulation the benefits are offset by long-term side effects. The original controlled, randomized, double-blind study reported more than 20 years ago showed benefits using prednisone [Mendell et al., N. Engl. J. Med., 320: 1592-1597 (1989)]. Subsequent reports showed equal efficacy using deflazacort, a sodium-sparing steroid [Biggar et al., J. Pediatr., 138: 45-50 (2001)]. Recent studies also demonstrate efficacy by exon skipping, prolonging walking distance on the 6MWT. Thus far, published clinical studies have reported benefit for only mutations where the reading frame is restored by skipping exon 51 [Cirak et al., Lancet, 378: 595-605 (2011) and Goemans et al., New Engl. J. Med. 364: 1513-1522 (2011)]. In the only report of a double blind, randomized treatment trial promising results were demonstrated with eteplirsen, a phosphorodiamidate morpholino oligomer (PMO). In all of these exon-skipping trials, the common denominator of findings has been a plateau in walking ability after an initial modest improvement.

See also, U.S. Patent Application Publication Nos. 2012/0077860 published Mar. 29, 2012; 2013/0072541 published Mar. 21, 2013; and 2013/0045538 published Feb. 21, 2013.

In contrast to the deletion mutations, DMD exon duplications account for around 5% of disease-causing mutations in unbiased samples of dystrophinopathy patients [Dent et al., Am. J. Med. Genet., 134(3): 295-298 (2005)], although in some catalogues of mutations the number of duplications is higher [including that published by the United Dystrophinopathy Project in Flanigan et al., Hum. Mutat., 30(12): 1657-1666 (2009), in which it was 11%].

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

An AAV8-like AAV termed rh.74 to deliver DNAs encoding various proteins. Xu et al., *Neuromuscular Disorders*, 17: 209-220 (2007) and Martin et al., *Am. J. Physiol. Cell. Physiol.*, 296: 476-488 (2009) relate to rh.74 expression of cytotoxic T cell GalNAc transferase for Duchenne muscular dystrophy. Rodino-Klapac et al., *Mol. Ther.*, 18(1): 109-117 (2010) describes AAV rh.74 expression of a micro-dystrophin FLAG protein tag fusion after delivery of the AAV rh.74 by vascular limb perfusion.

The muscular dystrophies are a group of diseases without identifiable treatment that gravely impact individuals, families, and communities. The costs are incalculable. Individuals suffer emotional strain and reduced quality of life associated with loss of self-esteem. Extreme physical challenges resulting from loss of limb function creates hardships in activities of daily living. Family dynamics suffer through financial loss and challenges to interpersonal relationships. Siblings of the affected feel estranged, and strife between spouses often leads to divorce, especially if responsibility for the muscular dystrophy can be laid at the feet of one of the parental partners. The burden of quest to find a cure often becomes a life-long, highly focused effort that detracts and challenges every aspect of life. Beyond the family, the community bears a financial burden through the need for added facilities to accommodate the handicaps of the muscular dystrophy population in special education, special transportation, and costs for recurrent hospitalizations to treat recurrent respiratory tract infections and cardiac complications. Financial responsibilities are shared by state and federal governmental agencies extending the responsibilities to the taxpaying community.

There thus remains a need in the art for treatments for muscular dystrophies including DMD.

DESCRIPTION

The present invention provides methods and products for preventing, delaying the progression of, and/or treating DMD involving a duplication of exon 2 of the DMD gene. The methods involve using AAV as a delivery vector for a polynucleotide construct encoding a U7 small nuclear RNA and an exon 2 targeting antisense sequence, an "exon 2-targeted U7snRNA polynucleotide construct" For example, the polynucleotide construct is inserted in the genome of a rAAV rh.74, the genome of a rAAV6 or the genome of a rAAV9. The polynucleotide sequence of the AAV rh.74 genome is shown in FIGS. 7A-7K and SEQ ID NO: 1.

Exemplary exon 2 targeting antisense sequences include, but are not limited to,

```
U7B
                                              (SEQ ID NO: 3)
TCAAAAGAAAACATTCACAAAATGGGTA;

U7Along
                                              (SEQ ID NO: 4)
GTTTTCTTTTGAAGATCTTCTCTTTCATcta;

U7Ashort
                                              (SEQ ID NO: 5)
AGATCTTCTCTTTCATcta;
and U7C
                                              (SEQ ID NO: 6)
GCACAATTTTCTAAGGTAAGAAT.
```

In one aspect, a method of ameliorating DMD in a patient is provided. In some embodiments, the method comprises the step of administering a rAAV to the patient, wherein the genome of the rAAV comprises an exon 2-targeted U7snRNA polynucleotide construct.

In yet another aspect, the invention provides a method of inhibiting the progression of dystrophic pathology associated with DMD. In some embodiments, the method comprises the step of administering a rAAV to the patient, wherein the genome of the rAAV comprises an exon 2-targeted U7snRNA polynucleotide construct.

In still another aspect, a method of improving muscle function in a patient afflicted with DMD is provided. In some embodiments, the method comprises the step of administering a rAAV to the patient, wherein the genome of the rAAV comprises an exon 2-targeted U7snRNA polynucleotide construct. In some instances, the improvement in muscle function is an improvement in muscle strength. The improvement in muscle strength is determined by techniques known in the art such as the maximal voluntary isometric contraction testing (MVICT). In some instances, the improvement in muscle function is an improvement in stability in standing and walking. The improvement in stability strength is determined by techniques known in the art such as the 6-minute walk test (6MWT) or timed stair climb.

In another aspect, the invention provides a method of delivering an exon 2-targeted U7snRNA polynucleotide construct to an animal (including, but not limited to, a human). In some embodiments, the method comprises the step of a rAAV to the patient, wherein the genome of the rAAV comprises an exon 2-targeted U7snRNA polynucleotide construct.

Cell transduction efficiencies of the methods of the invention described above and below may be at least about 60, 65, 70, 75, 80, 85, 90 or 95 percent.

In some embodiments of the foregoing methods of the invention, the virus genome is a self-complementary genome. In some embodiments of the methods, the genome of the rAAV lacks AAV rep and cap DNA. In some embodiments of the methods, the rAAV is a SC rAAV U7_ACCA comprising the exemplary genome set out in FIG. 9. In some embodiments the rAAV is a rAAV rh.74. In some embodiments, the rAAV is a rAAV6. In some embodiments, the rAAV is a rAAV9.

In yet another aspect, the invention provides a rAAV comprising the AAV rh.74 capsid and a genome comprising the exemplary exon 2-targeted U7 snRNA polynucleotide construct U7_ACCA. In some embodiments, the genome of the rAAV lacks AAV rep and cap DNA. In some embodiments, the rAAV comprises a self-complementary genome. In some embodiments of the methods, the rAAV is a SC rAAV U7_ACCA comprising the exemplary genome is set out in FIG. 9. In some embodiments the rAAV is a rAAV rh.74. In some embodiments, the rAAV is a rAAV6. In some embodiments, the rAAV is a rAAV9.

Recombinant AAV genomes of the invention comprise one or more AAV ITRs flanking at least one exon 2-targeted U7 snRNA polynucleotide construct Genomes with exon 2-targeted U7 snRNA polynucleotide constructs comprising each of the exon 2 targeting antisense sequences set out in paragraph [0012] are specifically contemplated, as well as genomes with exon 2-targeted U7 snRNA polynucleotide constructs comprising each possible combination of two or more of the exon 2 targeting antisense sequences set out in paragraph [0012]. In some embodiments, including the exemplified embodiments, the U7 snRNA polynucleotide includes its own promoter. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. As noted in the Background section above, the nucleotide sequences of the genomes of various AAV serotypes are known in the art. In some embodiments of the invention, the promoter DNAs are muscle-specific control elements, including, but not limited to, those derived from the actin and myosin gene families, such as from the myoD gene family [See Weintraub et al., *Science*, 251: 761-766 (1991)], the myocyte-specific enhancer binding factor MEF-2 [Cserjesi and Olson, *Mol. Cell. Biol.*, 11: 4854-4862 (1991)], control elements derived from the human skeletal actin gene [Muscat et al., *Mol. Cell. Biol.*, 7: 4089-4099 (1987)], the cardiac actin gene, muscle creatine kinase sequence elements [Johnson et al., *Mol. Cell. Biol.*, 9:3393-3399 (1989)] and the murine creatine kinase enhancer (MCK) element, desmin promoter, control elements derived from the skeletal fast-twitch troponin C gene, the slow-twitch cardiac troponin C gene and the slow-twitch troponin I gene: hypozia-inducible nuclear factors [Semenza et al., *Proc. Natl. Acad. Sci. USA*, 88: 5680-5684 (1991)], steroid-inducible elements and promoters including the glucocorticoid response element (GRE) [See Mader and White, *Proc. Natl. Acad. Sci. USA*, 90: 5603-5607 (1993)], and other control elements.

DNA plasmids of the invention comprise rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Use of cognate components is specifically contemplated. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, 1. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69 427-443 (2002); U.S. Pat. No. 6,566,118 and WO 98/09657.

In another embodiment, the invention contemplates compositions comprising rAAV of the present invention. Compositions of the invention comprise rAAV in a pharmaceutically acceptable carrier. The compositions may also comprise other ingredients such as diluents. Acceptable carriers and diluents are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Titers of rAAV to be administered in methods of the invention will vary depending, for example, on the particular rAAV, the mode of administration, the treatment goal, the individual, and the cell type(s) being targeted, and may be determined by methods standard in the art Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg) (i.e., $1\times10^7$ vg, $1\times10^8$ vg, $1\times10^9$ vg, $1\times10^{10}$ vg, $1\times10^{11}$ vg, $1\times10^{12}$ vg, $1\times10^{13}$ vg, $1\times10^{14}$ vg, respectively).

Methods of transducing a target cell (e.g., a skeletal muscle) with rAAV, in vivo or in vitro, are contemplated by the invention. The methods comprise the step of administering an effective dose, or effective multiple doses, of a composition comprising a rAAV of the invention to an animal (including a human being) in need thereof. If the dose is administered prior to development of DMD, the administration is prophylactic. If the dose is administered after the development of DMD, the administration is therapeutic. In embodiments of the invention, an effective dose is a dose that alleviates (eliminates or reduces) at least one symptom associated with DMD being treated, that slows or prevents progression to DMD, that slows or prevents progression of a disorder/disease state, that diminishes the extent of disease, that results in remission (partial or total) of disease, and/or that prolongs survival.

Administration of an effective dose of the compositions may be by routes standard in the art including, but not limited to, intramuscular, parenteral, intravenous, oral, buccal, nasal, pulmonary, intracranial, intraosseous, intraocular, rectal, or vaginal. Route(s) of administration and serotype(s) of AAV components of rAAV (in particular, the AAV ITRs and capsid protein) of the invention may be chosen and/or matched by those skilled in the art taking into account the infection and/or disease state being treated and the target cells/tissue(s). In some embodiments, the route of administration is intramuscular. In some embodiments, the route of administration is intravenous.

Combination therapies are also contemplated by the invention. Combination as used herein includes simultaneous treatment or sequential treatments. Combinations of methods of the invention with standard medical treatments (e.g., corticosteroids and/or immunosuppressive drugs) are specifically contemplated, as are combinations with other therapies such as those mentioned in the Background section above.

BRIEF DESCRIPTION OF THE DRAWING

FIGS. 1A-1F show histology and immunofluorescence analysis of muscles in the Dup2 mouse.

FIGS. 2A-2C show immunoblots from Western blot analysis of muscles in the Dup 2 mouse.

FIGS. 6A-6D presents results for exon-skipping experiments in vivo in which U7_ACCA SC rAAV was delivered by intramuscular injection in Dup2 mice.

FIGS. 7A-7K are the rh74 genome sequence (SEQ ID NO: 1) wherein nucleotides 210-2147 are the Rep 78 gene open reading frame, 882-208 are the Rep52 open reading frame, 2079-2081 are the Rep78 stop, 2145-2147 are the Rep78 stop, 1797-1800 are a splice donor site, 2094-2097 are a splice acceptor site, 2121-2124 are a splice acceptor site, 174-181 are the p5 promoter+1 predicted, 145-151 are the p5 TATA box, 758-761 are the p19 promoter+1 predicted, 732-738 are the p19 TATA box, 1711-1716 are the p40 TATA box, 2098-4314 are the VP1 Cap gene open reading frame, 2509-2511 are the VP2 start, 2707-2709 are the VP3 start and 4328-4333 are a polyA signal.

FIG. 9 shows the DNA sequence of the AAV genome insert (SEQ ID NO: 2) of the plasmid of FIG. 8.

EXAMPLES

Aspects and embodiments of the invention are illustrated by the following examples.

Example 1

Isolation of AAV rh.74

A unique AAV serotype was isolated from a rhesus macaque lymph node using a novel technique termed Linear Rolling Circle Amplification. Using the LRCA process, double-stranded circular AAV genomes were amplified from several rhesus macaques. The method is predicated on the ability to amplify circular AAV genomes by isothermic rolling circle amplification using phi29 phage DNA polymerase and AAV specific primers. LRCA products are contiguous head-to-tail arrays of the circular AAV genomes from which full-length AAV Rep-Cap molecular clones were isolated. Four isolates were sequenced and the predicted amino acid sequences for Rep and Cap ORFs were aligned and compared to previously published serotypes (Table). VP1 protein sequences were analyzed and revealed homology to the NHP AAV clades D, E, and AAV 4-like virus isolates. Analysis of the Rep78 (top portion of Table) ORF revealed strong homology to AAV 1 (98-99%).

TABLE 1

|       | AAV 1 | AAV 4 | AAV 7 | AAV 8 | rh.73 | rh.74 | rh.75 | rh.76 |
|-------|-------|-------|-------|-------|-------|-------|-------|-------|
| AAV 1 |       | 90    | 98    | 95    | 98    | 98    |       | 99    |
| AAV 4 | 63    |       | 90    | 87    | 90    | 90    |       | 90    |
| AAV 7 | 85    | 63    |       | 96    | 97    | 98    |       | 98    |
| AAV 8 | 84    | 63    | 88    |       | 97    | 97    |       | 95    |
| rh.73 | 79    | 61    | 83    | 80    |       | 99    |       | 99    |
| rh.74 | 84    | 63    | 88    | 93    | 80    |       |       | 99    |
| rh.75 | 65    | 82    | 82    | 64    | 62    | 64    |       |       |
| rh.76 | 85    | 63    | 91    | 86    | 84    | 86    | 84    |       |

Similarity of published AAV sequences and the new AAV sequences determined using one-pair alignment according to the Lipman-Pearson method implemented in the MegAlgn software in DNASTAR (DNASTAR Inc.) Light faced numbers (top, right) represent similarity in Rep78 sequences, whereas bold-faced numbers (lower, left) represent similarity in VP1 capsid sequences.

One macaque tissue sample (rh426-M) yielded a divergent AAV8-like isolate termed rh.74 that shares 93% sequence identity with AAV8. The nucleotide sequence of the rh.74 genome is set out in FIGS. 7A-7K and in SEQ ID NO: 1.

The rh.74 capsid gene sequence was cloned into an AAV helper plasmid containing the Rep gene from AAV2 to provide vector replication functions for recombinant AAV vector production.

Example 2

DMD Models

Examples of models of the DMD exon 2 duplication include in vivo and in vitro models as follows.

mdx$^{dup2}$ Mouse Model

Mice carrying a duplication of exon 2 within the Dmd locus were developed. The exon 2 duplication mutation is the most common human duplication mutation and results in relatively severe DMD.

Figure 10:
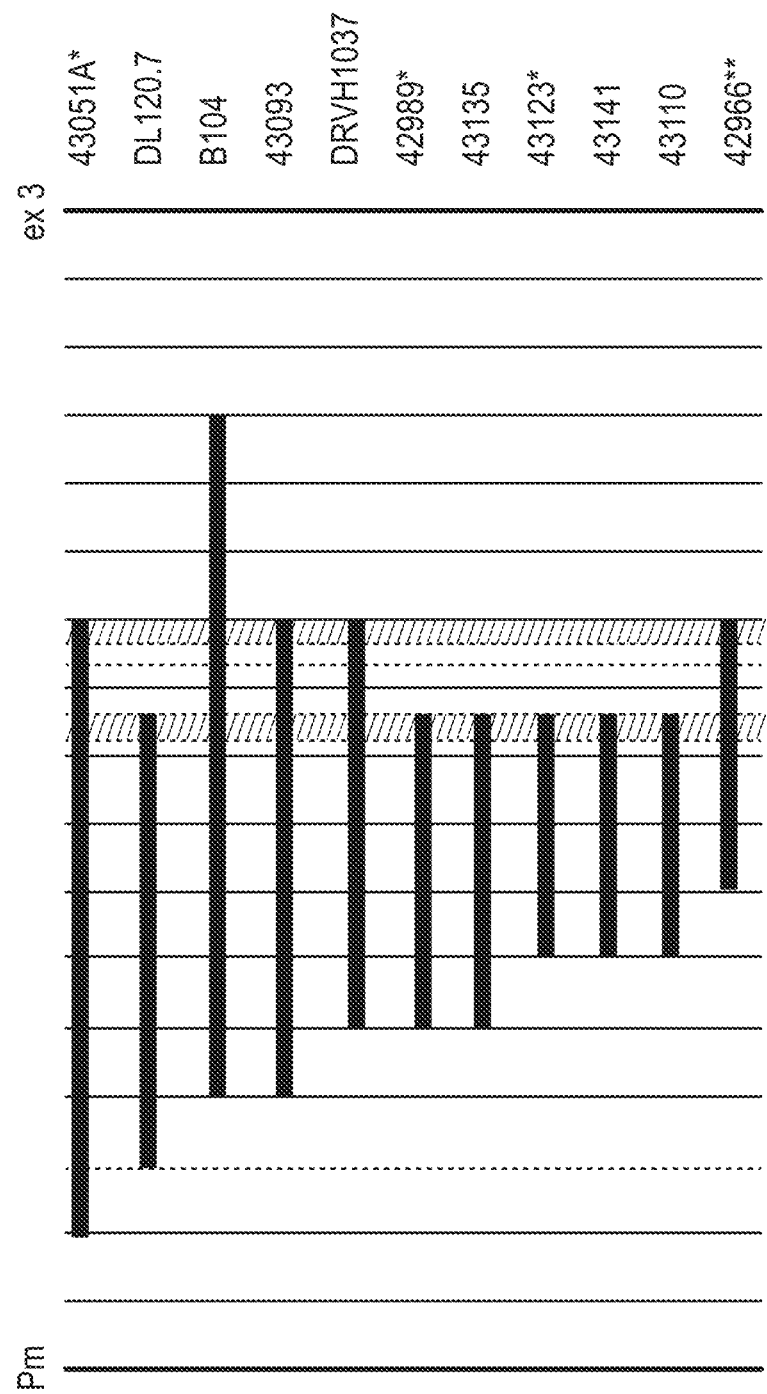
FIG. 10 shows vertical bars indicating the approximate position of an MLPA probe.

First, from White et al., Hum. Mutat, 27(9): 938-945 (2006), the maximum extent of the 11 different human exon 2 duplications was examined by MLPA and long-range PCR. Results are shown in FIG. 10. In FIG. 10, each vertical bar indicates the approximate position of an MLPA probe. The shaded columns indicate the two hotspot regions identified; they were used to determine the location of the insertion by homology of an exon 2 cassette in mouse.

Figure 11:
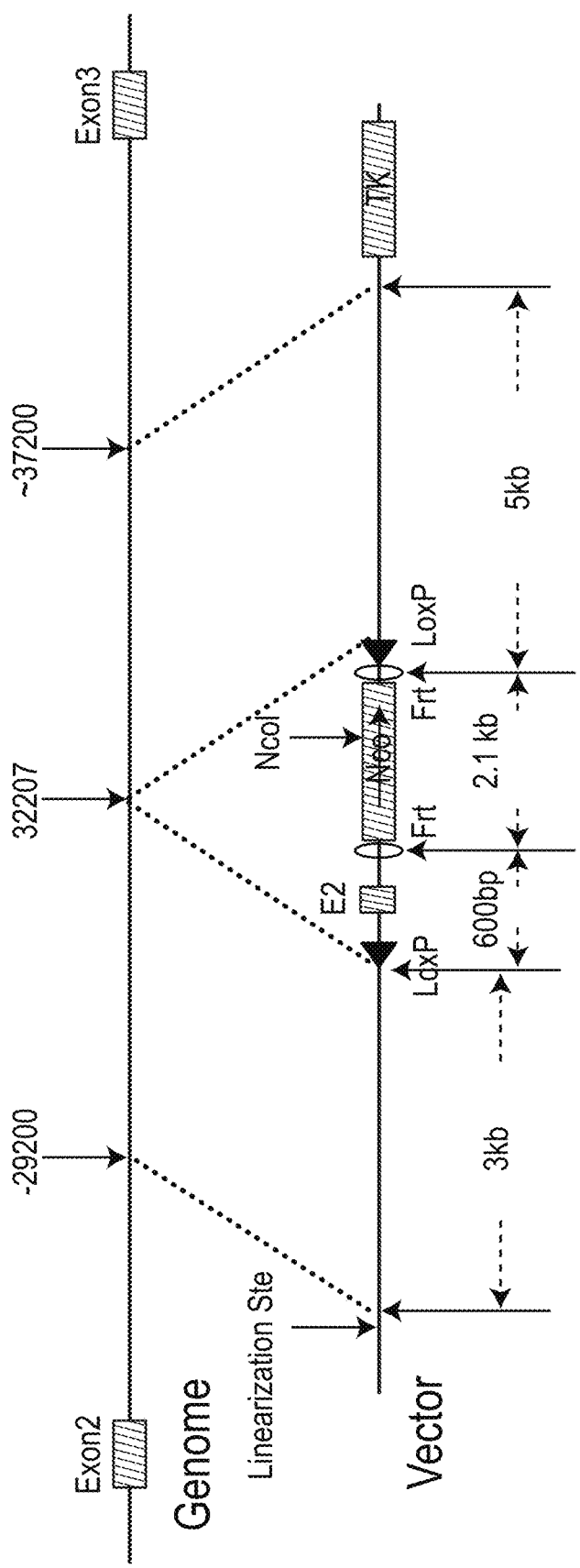
FIG. 11 shows a schematic of a vector used in creation of a mdx$^{dup2}$ (Dup2) mouse.

A map of the insertion vector is shown in FIG. 11. In the map, the numbers indicate the relative positions of cloning sites and exons and restriction sites. The neo cassette is in the same direction of the gene and the insertion point is precisely at 32207/32208 bp in the intron2. At least 150 bp extra intronic sequences are kept on each side of inserted exon 2, E2 region is 1775-2195 bp. Sizes of exon 2 and intron 2 are 62 bp and 209572 bp respectively.

Male C57BL/6 ES cells were transfected with the vector carrying the exon2 construct and then insertion was checked by PCR. One good clone was found, amplified and injected in dozens of albino BL/6 blastocysts. Injected blastocysts were implanted into recipient mice. The dystrophin gene from chimeric males was checked by PCR and then by RT-PCR. The colony was expanded and includes some female mice bred to homozygosity.

FIGS. 1A-1F and FIGS. 2A-2C demonstrate the dystrophin expression in muscles from a 4 week old hemizygous mdxdup2 mouse is essentially absent (As seen in FIGS. 2A-2C, traces of expression can be detected using an C-terminal antibody but not the exon 1-specific Manex1A antibody, consistent with a very small amount of translation from the exon 6 alternate translational initiation site we previously described.)

Immortalized and Conditionally Inducible fibroMyoD Cell Lines

Expression of the MyoD gene in mammalian fibroblasts results in transdifferentiation of cells into the myogenic lineage. Such cells can be further differentiated into myotubes, and they express muscle genes, including the DMD gene.

Immortalized cell lines that conditionally express MyoD under the control of a tetracycline-inducible promoter were generated. This is achieved by stable transfection of the primary fibroblast lines of a lentivirus the tet-inducible MyoD and containing the human telomerase gene (TER). The resultant stable line allows MyoD expression to be initiated by treatment with doxycycline. Such cell lines were generated from patients with DMD who carry a duplication of exon 2.

Figure 3:
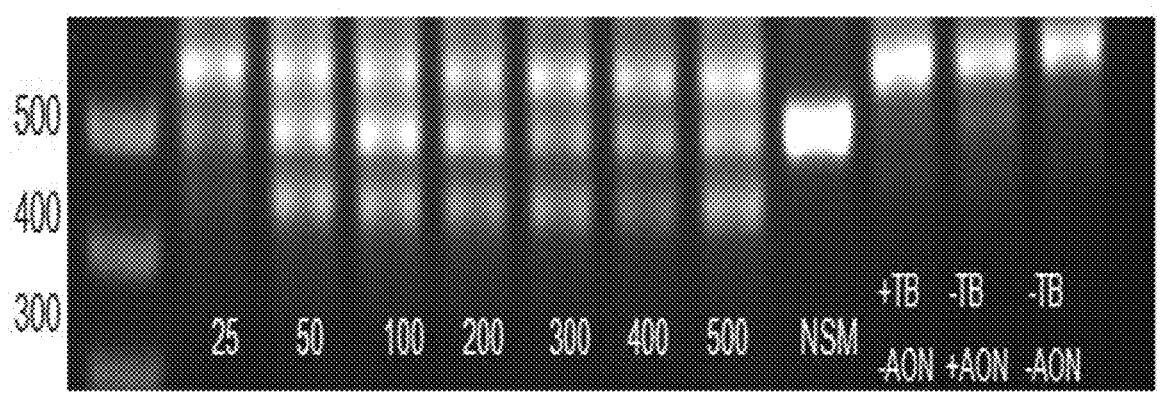
FIG. 3 shows that skipping of a duplicated exon 2 in a MyoD-transdifferentiated myoblast induced by an AON directed at an exon splice enhancer results in 39% wild type transcript. Dosage per lane shown in nMoles (25, 50, 100, 200, 300, 400, 500). The amount of the varying transcripts are shown under each lane, with the maximum shaded. TB=transfection buffer. NSM=normal skeletal muscle. The percentage of exon 2 duplication, wt, and exon 2 deletion is listed below each lane.

Using the line, duplication skipping using 2'-O-methyl antisense oligomers (AONs) provided by Dr. Steve Wilton (Perth, Australia) was demonstrated. Multiple cell lines were tested. Results from exemplary cells lines are shown in FIG. 3.

Transiently MyoD-Transfected Primary Cell Lines

Proof-of-principle experiments using primary fibroblast lines transiently transfected with adenovirus-MyoD were conducted. The adenovirus constructs were not integrated in the cell genomes, yet MyoD was transiently expressed. The resulting DMD expression was sufficient to perform exon skipping experiments (although reproducibility favors the stably transfected lines.)

Example 3

Effectiveness of U7 snRNA-Mediated Skipping on Exon 2 Duplication Mutations

Products and methods for virally-mediated exon skipping of duplicated exons were developed. The products and methods were modified compared to the U7snRNA systems described in Goyenvalle et al., Science, 306(5702): 1796-1799 (2004) or Goyenvalle et al., Mol. Ther., 20(6): 179601799 (2004).

Figure 4:
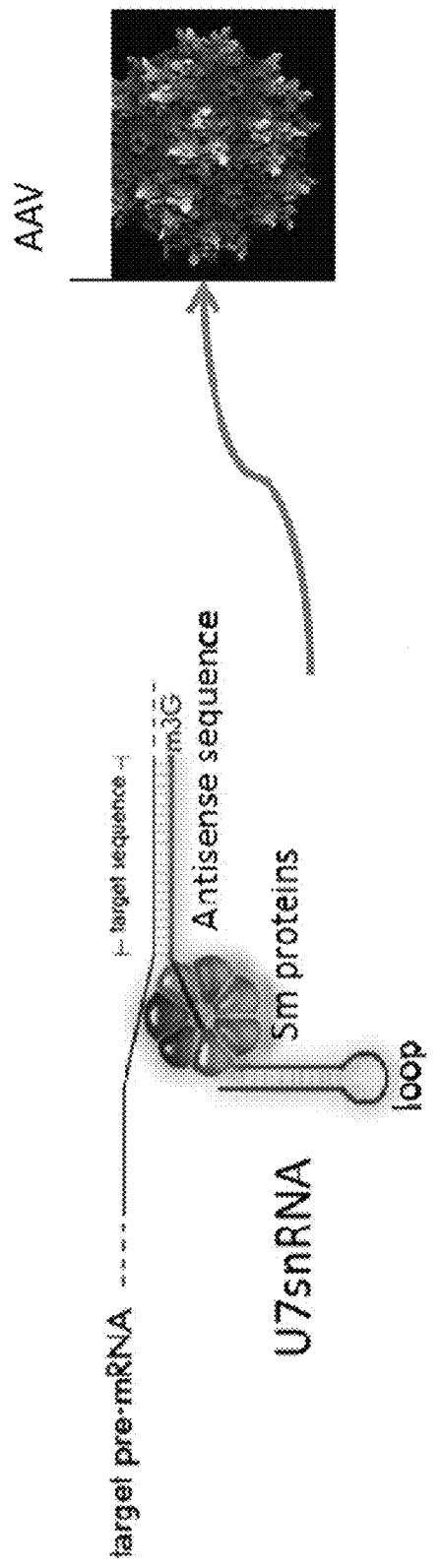
FIG. 4 illustrates the U7snRNA vector approach to exon skipping. U7snRNA is used as a carrier to target the pre-messenger RNA. It is composed of a loop used for the nucleocytoplasmic export, a recognition sequence to bind the Sm proteins used for an efficient assembly between the U7snRNA and the target pre-mRNA and an antisense sequence to target the pre-mRNA. It has its own promoter and 3' downstream sequences. The U7 cassette is then cloned in an AAV plasmid, to produce the vector.

U7snRNA was modified to include a target antisense sequence to interfere with splicing at a given target exon (FIG. 4). Specifically, four new exon 2 targeting sequences were designed based upon the results of the AON studies described in Example 2.

U7B
(SEQ ID NO: 3)
TCAAAAGAAAACATTCACAAAATGGGTA

U7Along
(SEQ ID NO: 4)
GTTTTCTTTTGAAGATCTTCTCTTTCATcta

U7Ashort
(SEQ ID NO: 5)
AGATCTTCTCTTTCATcta

U7C
(SEQ ID NO: 6)
GCACAATTTTCTAAGGTAAGAAT

U7 snRNA constructs including the exon 2 target sequences were generated. Each U7 snRNA construct included one of the target sequences. U7 snRNA constructs targeted to selected other exons were also generated (based upon MyoD-transdifferentiated cell line studies, above). Self complementary (SC) AAV vectors with genomes including one or more of the U7 snRNA constructs were then produced.

For experiments in cell culture and for intramuscular injection in Dup2 mice, rAAV1 vectors were utilized. Recombinant SC AAV vectors of a desired AAV serotype were produced by a modified cross-packaging approach using a plasmid comprising a desired vector genome by an adenovirus-free, triple plasmid DNA transfection ($CaPO_4$ precipitation) method in HEK293 cells [Rabinowitz et al., *J. Virol.*, 76:791-801 (2002)]. Vector was produced by co-transfecting with an AAV helper plasmid and an adenovirus helper plasmid in similar fashion as that previously described [Wang et al., *Gene. Ther.*, 10:1528-1534 (2003)]. The adenovirus helper plasmid (pAdhelper) expresses the adenovirus type 5 E2A, E4ORF6, and VA I/II RNA genes which are required for high-titer rAAV production.

Vectors were purified from clarified 293 cell lysates by sequential iodixanol gradient purification and anion-exchange column chromatography using a linear NaCl salt gradient as previously described [Clark et al., *Hum. Gene Ther*, 10:1031-1039 (1999)]. Vector genome (vg) titers were measured using QPCR based detection with a specific primer/probe set utilizing the Prism 7500 Taqman detector system (PE Applied Biosystems) as previously described (Clark et al., supra). Vector stock titers ranged between $1-10 \times 10^{12}$ vg/mL.

Initial exon-skipping analysis was by RT-PCR using the SC rAAV vectors to transduce Dup2 immortalized human fibromyoblasts. Dup 2 immortalized human fibroblasts that were able to transdifferentiate into muscle lineage cells under the control of doxycycline were produced by transduction with both telomerase-expressing and tet-inducible-MyoD expressing vectors. The converted human fibromyoblasts (FM) were then transduced with the SC rAAV carrying different U7 constructs incorporating exon 2 antisense sequences.

Figure 5:
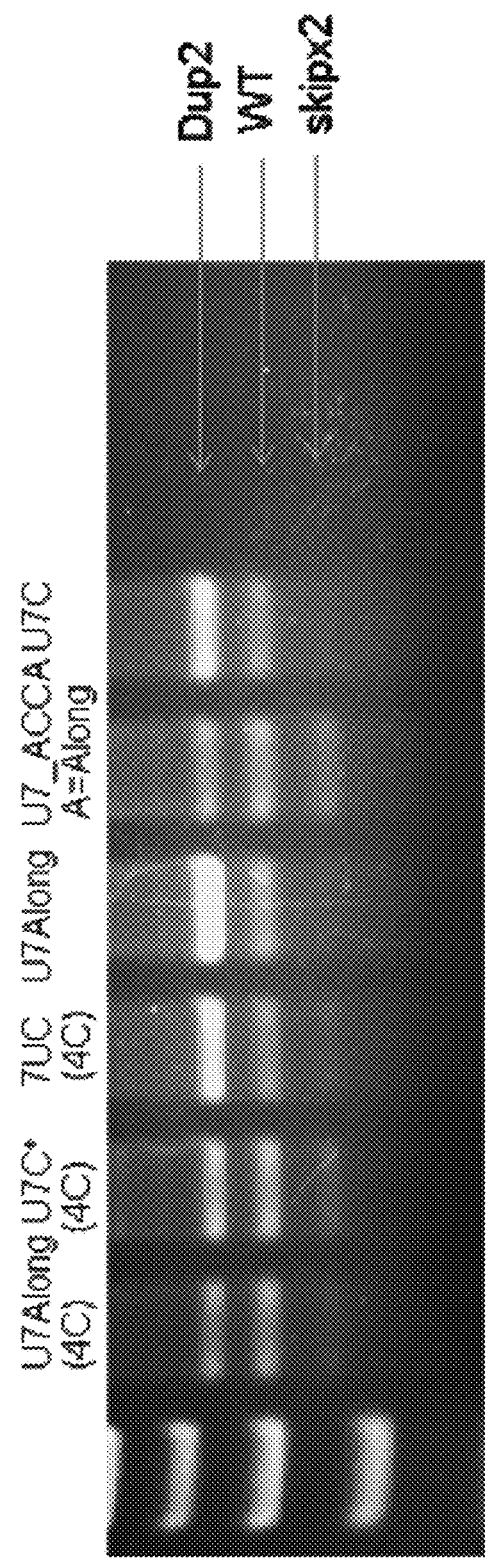
FIG. 5 shows RT-PCR results for exon-skipping experiments using SC rAAV vectors to transduce Dup2 immortalized human fibromyoblasts with exemplary exon 2-targeted U7snRNA constructs.
Figure 8:
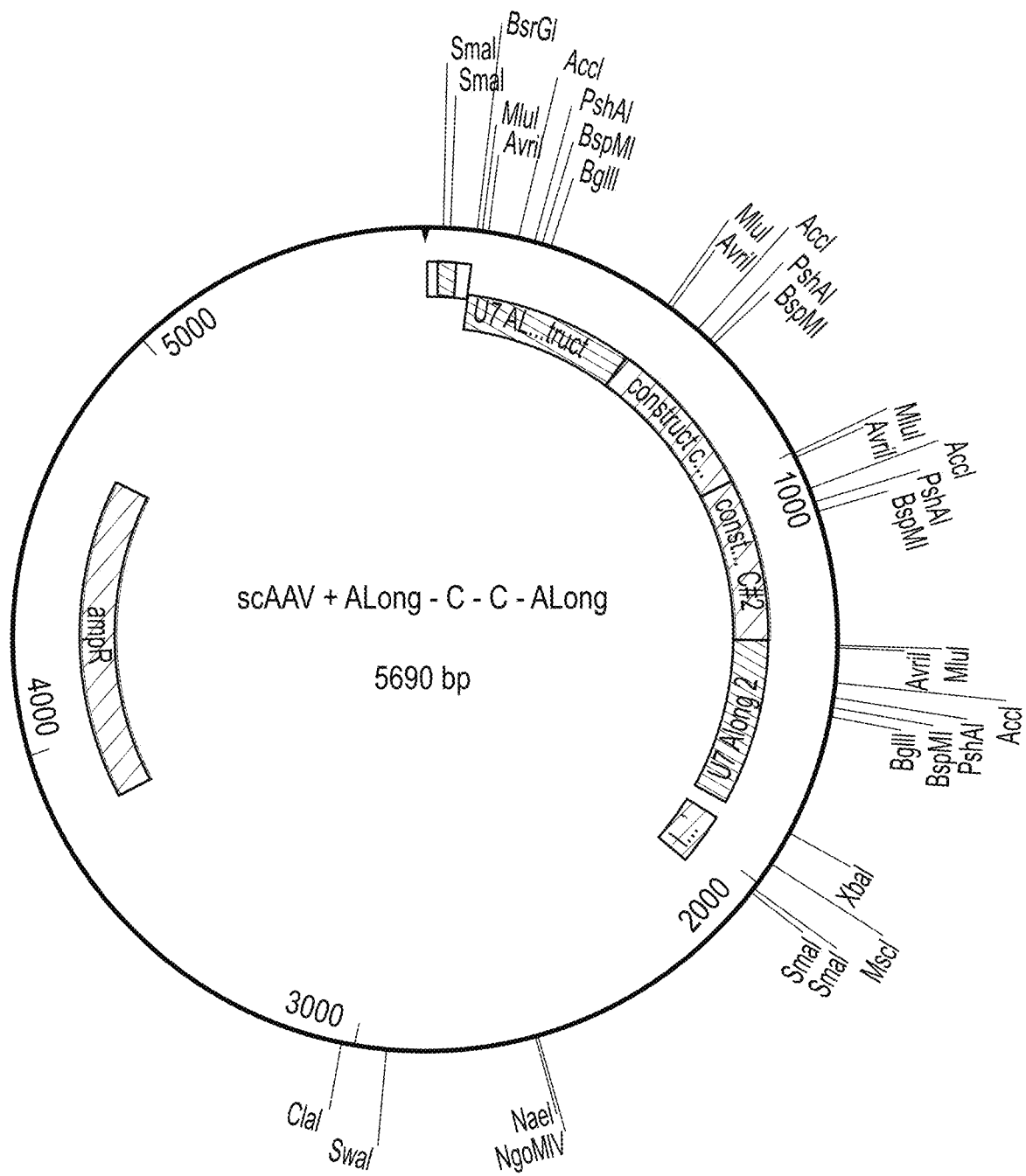
FIG. 8 shows a map of a plasmid with an AAV genome insert of an exemplary exon 2-targeted U7snRNA.

RT-PCR results are shown in FIG. 5 for SC rAAV.1-U7 constructs with three different antisense sequences. In FIG. 5, "(4C)" indicates four copies of the U7 construct were included in a vector genome, "+" indicates a higher dose and "U7_ACCA A=Along" indicates a vector genome (shown in a plasmid map in FIG. 8 and the sequence of which, SEQ ID NO: 2, is set out in FIG. 9) comprising in sequence four exon 2-targeted U7 snRNA polynucleotide constructs: a first U7Along construct, a first U7C construct, a second U7C construct and a second U7Along construct. As shown, the U7_ACCA A-Along SC rAAV (abbreviated U7_ACCA SC rAAV1 elsewhere herein) achieved a higher percentage of exon 2 skipping in comparison to any other vector construct.

In subsequent experiments, exon-skipping efficiency was analyzed in vivo. The most efficient AAV-U7 vector, U7_ACCA SC rAAV1, was chosen for intramuscular injection in Dup2 mice. Results are shown below in FIGS. 6A-6D wherein (FIG. 6A) shows dystrophin staining where the protein expression is restored, and is properly localized at the membrane in many muscle fibers; (FIG. 6B) protein restoration was confirmed by western blot RT-PCR shows (FIG. 6C) dose-dependent single or double skipping in Dup2 mice, as well as (FIG. 6D) efficient skipping in the wild-type mouse.

Thus, a highly efficient AAV-mediated U7snRNA was designed to skip exon 2 allowing subsarcolemmal dystrophin restoration. Cardiac function; EDL and diaphragm force assessments; and treadmill and grip tests will be compared between untreated and treated mice.

Based upon the degree of dystrophin expression detectable within the injected muscle, U7_ACCA SC rAAV was chosen for further experiments to be delivered intraveneously to a first cohort at 1E11 vg/kg, followed by dosing one log higher in a second cohort Injection will be performed at four weeks, and animals evaluated by physiologic assessment and histopathology at 10 and 24 weeks (n=8 animals per cohort) as described above.

Example 4

Intramuscular Delivery of U7-ACCA by AAV1 Results in Significant N-Truncated Dystrophin Expression in Dup2 Mice A rAAV1 comprising the genome insert of FIG. 9 was produced by the methods described in Example 3. The AAV.1U7-ACCA was then administered to Dup2 mice via intramuscular injection.

Figure 12A:
FIGS. 12A-12E show the results of intramuscular delivery to Dup2 mice of AAV1 U7-ACCA.

RT-PCR performed on DMD mRNA 4 weeks after TA intramuscular injection of 5e11vg AAV.1U7-ACCA showed nearly complete skipping of both copies of exon 2 in Dup2 animals [FIG. 12A].

Figure 12B:
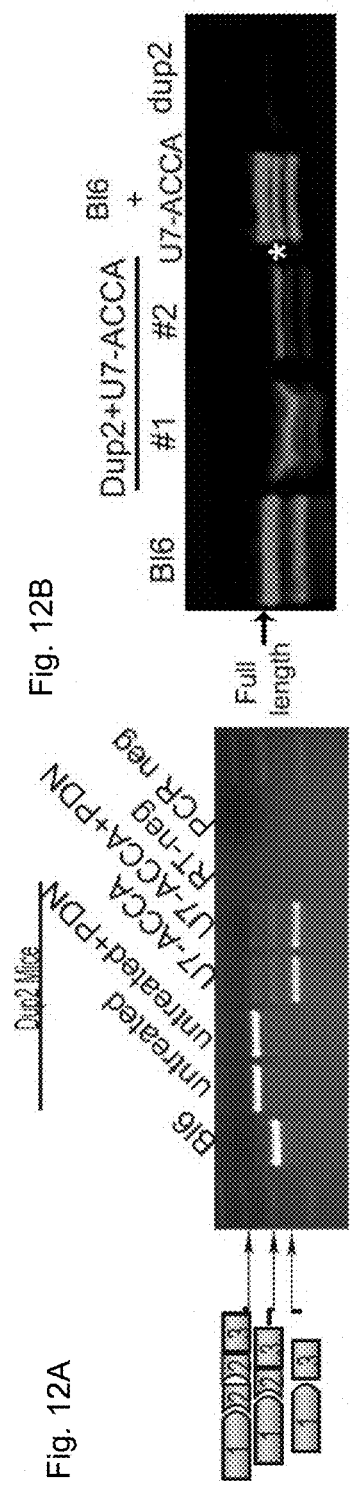

Immunoblot using a C-terminal antibody (PA1-21011, ThermoScientific) performed a month after infection showed significant expression of the N-truncated isoform (asterisk) in both Dup2 and control Bl6 mice [FIG. 12B]. The protein induced in Bl6 males injected with U7-ACCA was of the same size as that expressed in the Dup2 treated animals, confirming the size difference between this protein and the full-length isoform.

Figure 12C:
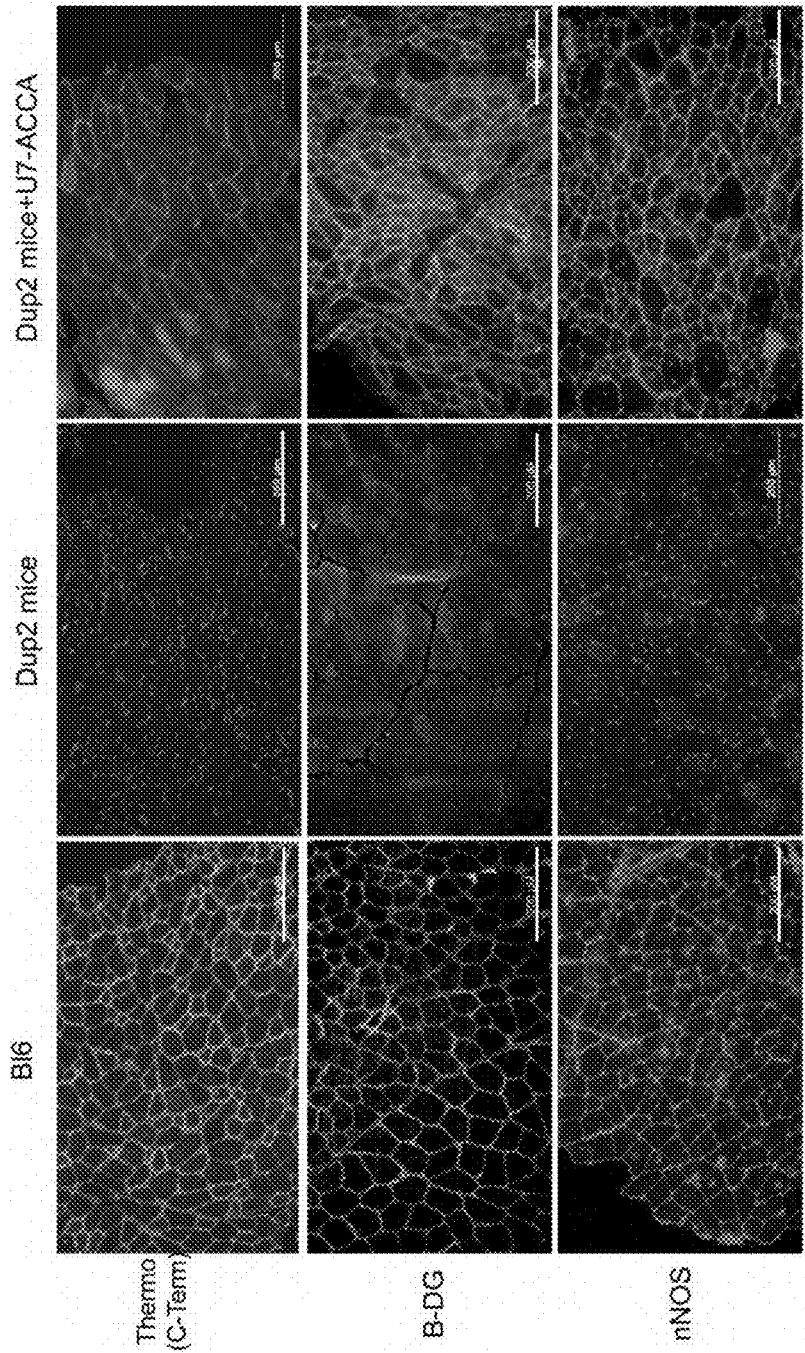

Immunofluorescent staining of dystrophin, β-dystroglycan, and neuronal nitric oxide synthase demonstrated restoration of members of the dystrophin associated complex [FIG. 12C].

Figure 12D:
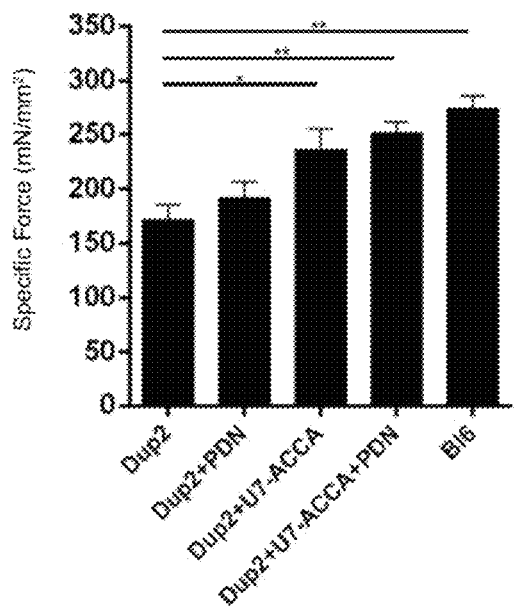

Normalized specific force following tetanic contraction in untreated Dup2 animals was significantly less than in Bl6 mice Intramuscular injection of AAV1.U7-ACCA, either alone or with prednisone, significantly increased force to levels that were not significantly different from that seen in Bl6 mice. No significant difference was observed between untreated Dup2 mice and those treated with prednisone along (Dup2+PDN) [FIG. 12D]. For this assay, normalized specific force was evaluated using a published protocol [Hakim et al., *Journal of Applied Physiology*, 110: 1656-1663 (2011)].

Figure 12E:
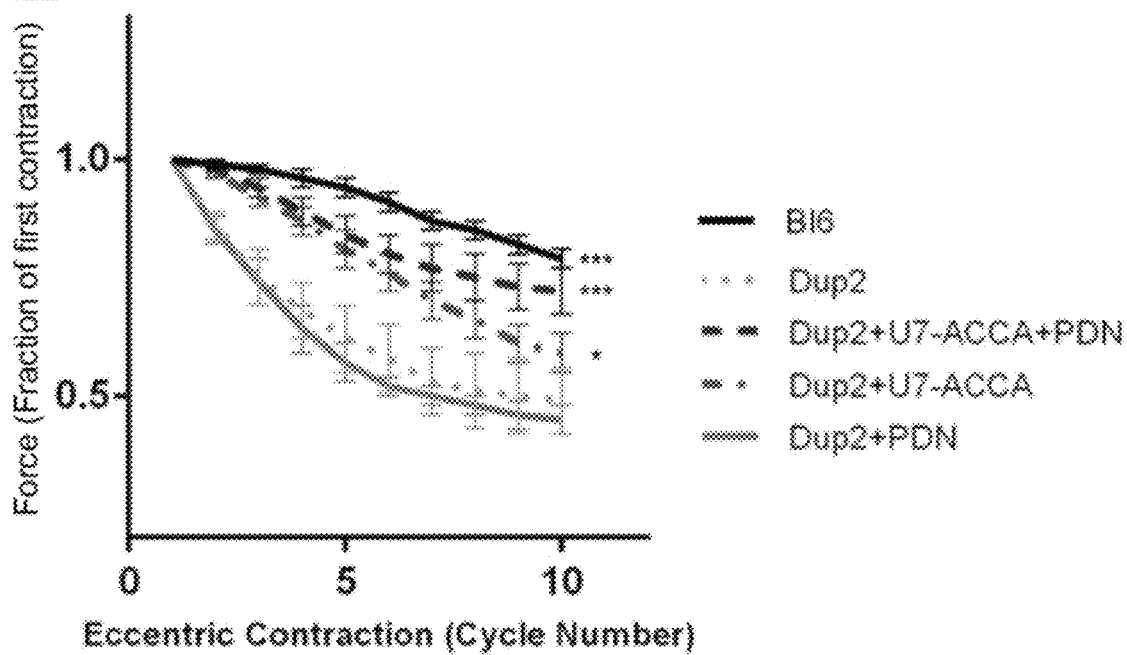

Treatment significantly protected Dup2 muscle from loss of force following repetitive eccentric contractions, as assessed by published protocols (Hakim et al., supra). Treatment of Dup2 mice with AAV1.U7-ACCA alone resulted in a statistically significant improvement compared to untreated Dup2 mice. The combination of AAV1.U7-ACCA and prednisone resulted in no significant difference in comparison to control Bl6 mice in force retention following contractions #3 to #10 [FIG. 12E].

Example 5

Intravenous Injection of AAV9-U7_ACCA in the Dup2 Mouse Model Results in Significant Expression of the N-Truncated Isoform and Correction of Strength Deficit Based upon the degree of dystrophin expression detectable within injected muscle, we chose to deliver U7_ACCA SC rAAV intravenously for further experiments, and selected the serotype rAAV9 based upon known tissue distribution properties.

A rAAV9 comprising the genome insert of FIG. 9 was produced by the methods described in Example 3. The AAV.9U7-ACCA was then administered to Dup2 mice. A first cohort was injected via tail vein with 3.3E112 vg/kg. Injection was performed at four weeks of age.

Figure 13A:
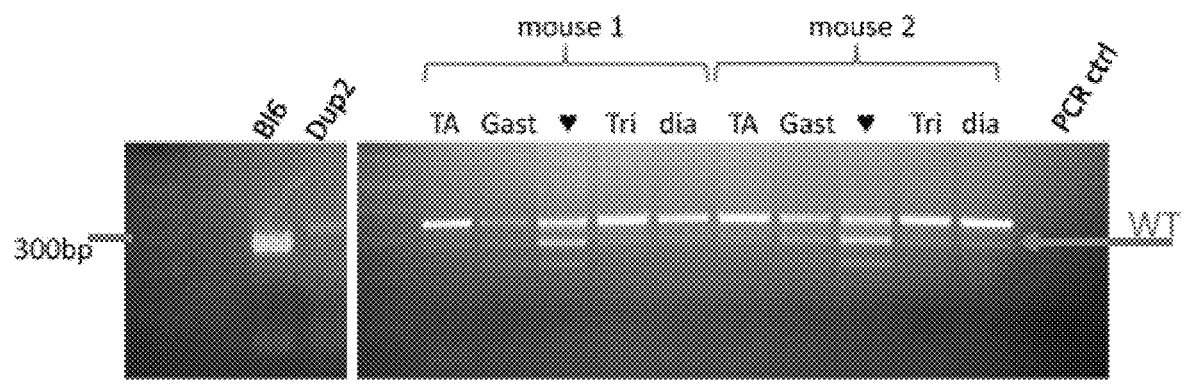
FIGS. 13A-13F show the results of intravenous injection of AAV9 U7_ACCA in the Dup2 mouse model.

RT-PCR was performed on five different Dup2 mouse muscles one month after tail vein injection of AAV9.U7-ACCA (3.3E12 vg/kg) [FIG. 13A]. As demonstrated by the presence of multiple transcripts (labeled Dup2, wt, and De12), U7-ACCA treatment was able to force skipping of one or both copies of exon 2 in all muscles tested. (TA: tibialis anterior; Gas: gastrocnemius; ♥: heart; Tri: triceps; dia: diaphragm.)

Figure 13B:
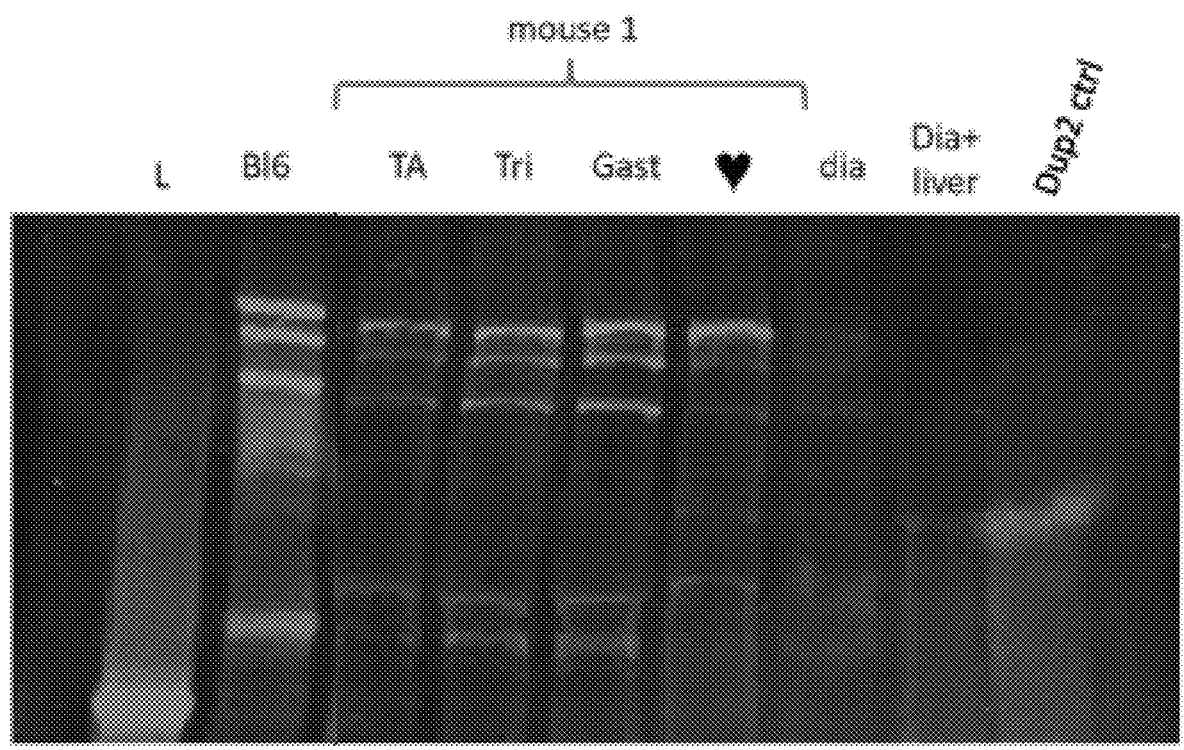

Western blot using a C-terminal antibody (PA1-21011, ThermoScientific) performed on five different muscles one month after injection demonstrated the presence of dystrophin in all tested muscles[FIG. 13B].

Figure 13C:
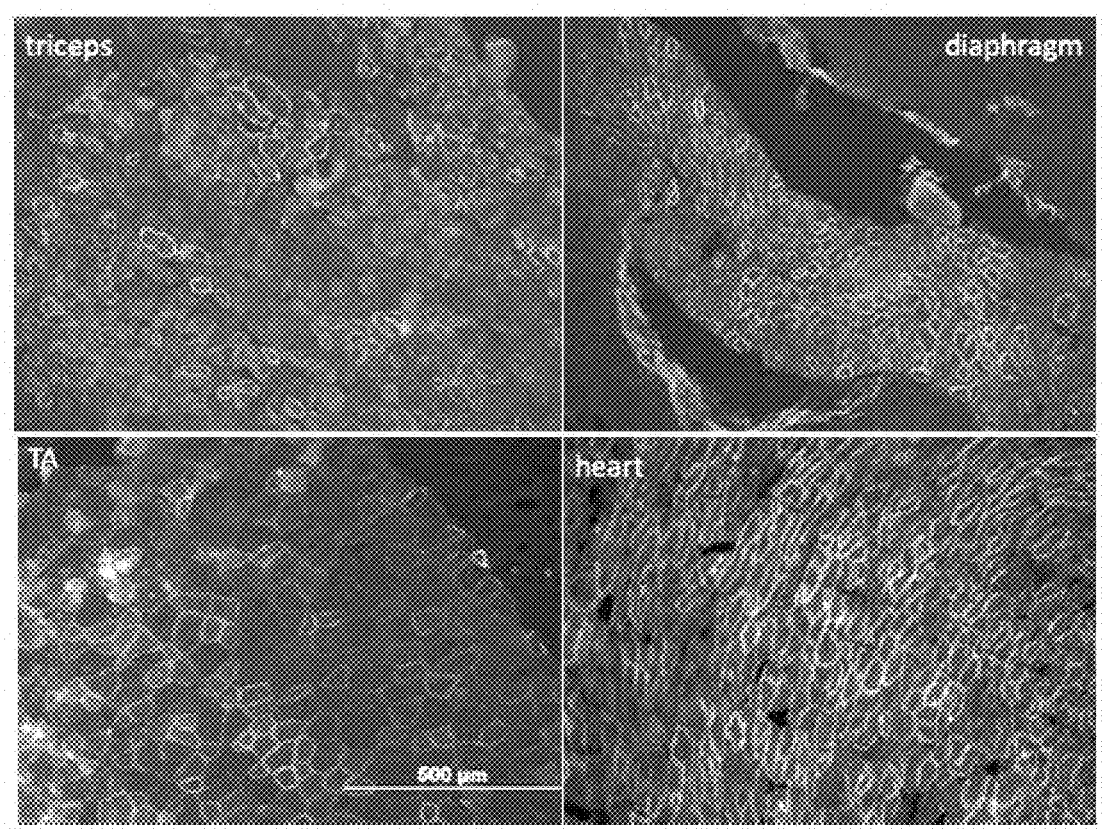

Immunostaining using a C-terminal antibody (PA1-21011, ThermoScientific) of dystrophin on the same samples confirmed dystrophin expression and its proper localization at the sarcolemma [FIG. 13C].

Figure 13D:
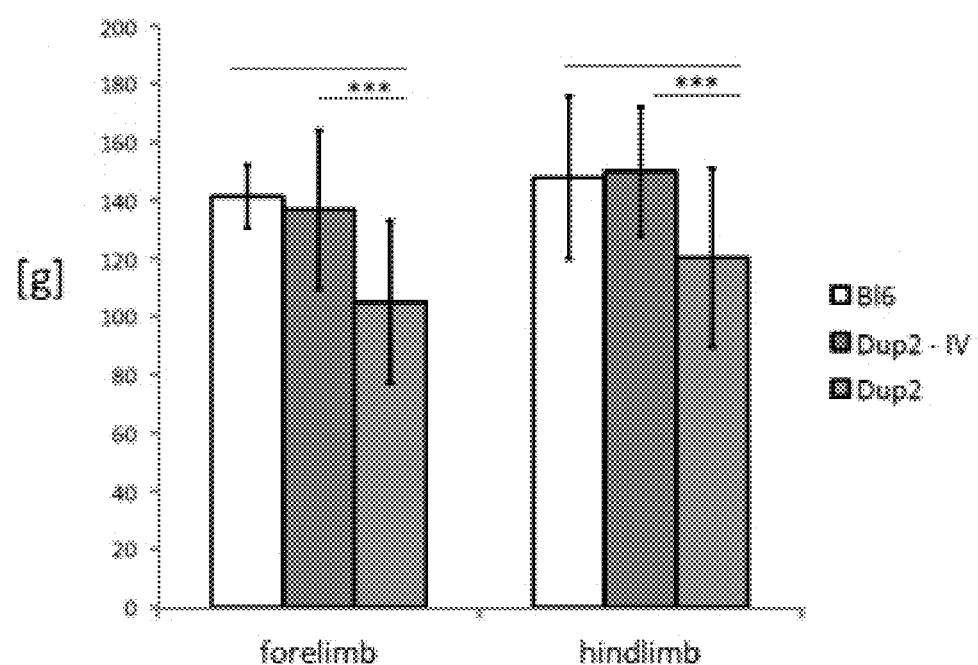

Evaluation of both forelimb and hindlimb grip strength demonstrated a complete correction of grip strength in Dup2 animals treated with AAV9.U7-ACCA [FIG. 13D]. This assay was performed using a published protocol [Spurney, et al., *Muscle & Nerve*, 39, 591-602 (2009)].

Figure 13E:
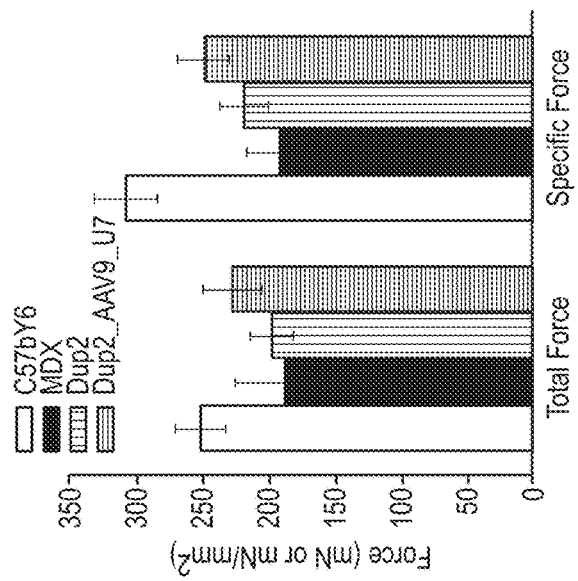

Normalized specific and total forces following tetanic contraction showed improvement in muscle force in comparison to untreated Dup2 animals [FIG. 13E], using a published protocol [Hakim et al., supra).

Figure 13F:
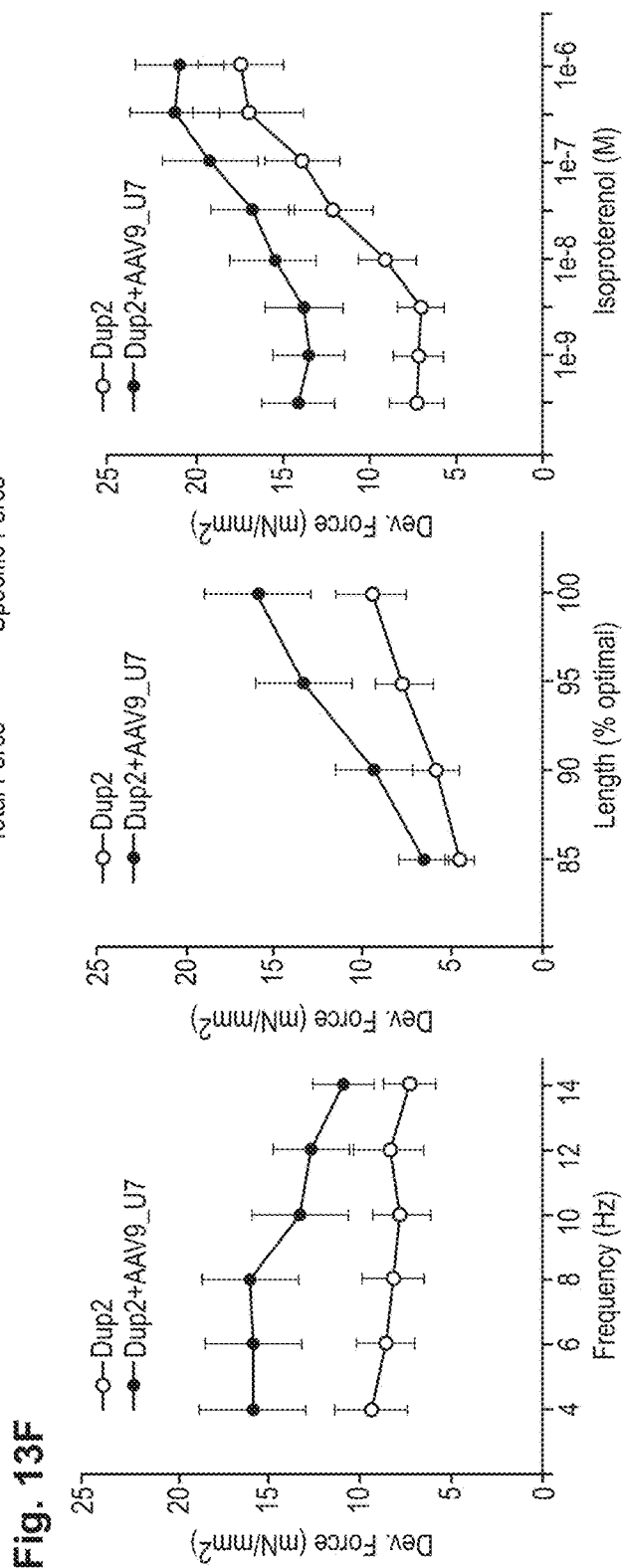

Cardiac papillary muscles demonstrated improvements in length-dependent force generation in treated animals [FIG. 13F], using a published protocol [Janssen et al., *Am J Physiol Heart Circ Physiol.*, 289(6):H2373-2378 (2005)].

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety with particular attention to the content for which they are referred.

We claim:

1. A recombinant adeno-associated virus (rAAV) comprising a genome comprising at least one Duchenne Muscular Dystrophy (DMD) exon 2-targeted U7snRNA polynucleotide construct, wherein the at least one DMD exon 2-targeted U7snRNA polynucleotide construct comprises the nucleotide sequence of any one of SEQ ID NOs: 4, 5, 7 and 8.

2. The rAAV of claim 1 wherein the at least one DMD exon 2-targeted U7snRNA polynucleotide construct comprises the nucleotide sequence of SEQ ID NO: 7.

3. The rAAV of claim 1 wherein the at least one DMD exon 2-targeted U7snRNA polynucleotide construct comprises the nucleotide sequence of SEQ ID NO: 8.

4. The rAAV of claim 1 wherein the at least one DMD exon 2-targeted U7snRNA polynucleotide construct comprises two or more nucleotide sequences, each sequence comprising SEQ ID NO: 7.

5. The rAAV of claim 1 wherein the at least one DMD exon 2-targeted U7snRNA polynucleotide construct comprises two or more nucleotide sequences, each sequence comprising SEQ ID NO: 8.

6. The rAAV of claim 1 wherein the at least one DMD exon 2-targeted U7snRNA polynucleotide construct comprises two or more nucleotide sequences comprising the nucleotide sequence of SEQ ID NO: 7 and/or SEQ ID NO: 8.

7. The rAAV of claim 1 wherein the genome comprises in sequence four exon 2-targeted U7snRNA polynucleotide constructs comprising a first U7Along nucleotide sequence comprising SEQ ID NO: 7, a first U7C nucleotide sequence comprising SEQ ID NO: 8, a second U7C nucleotide sequence comprising SEQ ID NO: 8, and a second U7Along nucleotide sequence comprising SEQ ID NO: 7.

8. The rAAV of claim 1 wherein the at least one DMD exon 2-targeted U7snRNA polynucleotide construct comprises at least one nucleotide sequence comprising SEQ ID NO: 4 or 5.

9. The rAAV of claim 1 wherein the at least one DMD exon 2-targeted U7snRNA polynucleotide construct comprises two or more nucleotide sequences comprising SEQ ID NO: 4 or 5.

10. The rAAV of claim 1 wherein the genome is a self-complementary genome and/or a single-stranded genome.

11. The rAAV of claim 1 wherein the rAAV is rAAV rh.74, rAAV-1, rAAV-2, rAAV-3, rAAV-4, rAAV-5, rAAV-6, rAAV-7, rAAV-8, rAAV-9, rAAV-10, or rAAV-11.

12. The rAAV of claim 11 wherein the rAAV is rAAV rh.74, rAAV-8, or rAAV-9.

13. The rAAV of claim 1 wherein the genome of the rAAV lacks AAV rep and cap DNA.

14. The rAAV of claim 1 further comprising an AAV rh.74 capsid, an AAV-1 capsid, an AAV-2 capsid, an AAV-3 capsid, an AAV-4 capsid, an AAV-5 capsid, an AAV-6 capsid, an AAV-7 capsid, an AAV-8 capsid, an AAV-9 capsid, an AAV-10 capsid, or an AAV-11 capsid.

15. The rAAV of claim 1 wherein the at least one DMD exon 2-targeted U7snRNA polynucleotide construct comprises two or more nucleotide sequences, each sequence comprising SEQ ID NO: 4.

16. The rAAV of claim 1 wherein the at least one DMD exon 2-targeted U7snRNA polynucleotide construct comprises two or more nucleotide sequences, each sequence comprising SEQ ID NO: 5.

17. A composition comprising the rAAV of claim 1 and a carrier or diluent.

* * * * *